United States Patent
St. Pierre

(10) Patent No.: US 12,186,125 B2
(45) Date of Patent: Jan. 7, 2025

(54) BREAST ULTRASOUND WORKFLOW APPLICATION

(71) Applicant: HOLOGIC, INC., Marlborough, MA (US)

(72) Inventor: Shawn St. Pierre, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/979,964

(22) PCT Filed: May 7, 2019

(86) PCT No.: PCT/US2019/031094
§ 371 (c)(1),
(2) Date: Sep. 11, 2020

(87) PCT Pub. No.: WO2019/217405
PCT Pub. Date: Nov. 14, 2019

(65) Prior Publication Data
US 2021/0015447 A1   Jan. 21, 2021

Related U.S. Application Data

(60) Provisional application No. 62/668,078, filed on May 7, 2018.

(51) Int. Cl.
*A61B 8/08* (2006.01)
*A61B 8/00* (2006.01)
(Continued)

(52) U.S. Cl.
CPC .......... *A61B 8/0825* (2013.01); *A61B 8/0841* (2013.01); *A61B 8/085* (2013.01);
(Continued)

(58) Field of Classification Search
CPC ..... A61B 8/0825; A61B 8/0841; A61B 8/085; A61B 8/14; A61B 8/463; A61B 10/0233;
(Continued)

(56) References Cited

U.S. PATENT DOCUMENTS

2010/0150417 A1   6/2010   Kshirsagar
2011/0208052 A1   8/2011   Entrekin
(Continued)

FOREIGN PATENT DOCUMENTS

CN   101604458 A   12/2009
JP   H-06335456 A   12/1994
(Continued)

OTHER PUBLICATIONS

International Search Report and Written Opinion of the International Searching Authority for International Patent Application No. PCT/US2019/031094 mailed Aug. 30, 2019, 15 pages.
(Continued)

*Primary Examiner* — Sean D Mattson
*Assistant Examiner* — Michael Yiming Fang
(74) *Attorney, Agent, or Firm* — Merchant & Gould P.C.

(57) ABSTRACT

Methods and system for providing an ultrasound workflow tool that facilitates performing a diagnostic exam, an interventional procedure, and an excision surgery. The ultrasound workflow tool is an application that executes on a computing device, and is used in connection with a wired or wireless ultrasound device.

9 Claims, 25 Drawing Sheets

(51) Int. Cl.
*A61B 8/14* (2006.01)
*A61B 10/02* (2006.01)

(52) U.S. Cl.
CPC .............. *A61B 8/14* (2013.01); *A61B 8/463* (2013.01); *A61B 10/0233* (2013.01)

(58) Field of Classification Search
CPC ....... A61B 8/469; A61B 8/5223; A61B 8/461; A61B 10/0041; G16H 50/30
See application file for complete search history.

(56) References Cited

U.S. PATENT DOCUMENTS

| | | | | |
|---|---|---|---|---|
| 2014/0033126 | A1* | 1/2014 | Kreeger | G06T 11/003 715/833 |
| 2014/0180106 | A1* | 6/2014 | Takahashi | A61B 8/467 600/443 |
| 2014/0221835 | A1* | 8/2014 | Ota | A61B 8/463 600/443 |
| 2016/0067007 | A1* | 3/2016 | Piron | G16H 20/40 705/3 |
| 2016/0155247 | A1* | 6/2016 | Robinson | A61B 8/0825 382/131 |
| 2017/0235903 | A1* | 8/2017 | McLaughlin | A61B 8/461 715/708 |
| 2017/0258438 | A1* | 9/2017 | Kanayama | G01S 7/52071 |
| 2018/0000453 | A1 | 1/2018 | Hunter et al. | |
| 2018/0053300 | A1* | 2/2018 | Podilchuk | G06T 7/0016 |
| 2018/0157928 | A1* | 6/2018 | Oliveira | G16H 30/40 |
| 2018/0342060 | A1* | 11/2018 | Yao | G06F 3/167 |
| 2019/0200960 | A1* | 7/2019 | Kang | A61B 8/54 |
| 2020/0359991 | A1* | 11/2020 | Xu | G16H 50/30 |
| 2021/0004960 | A1* | 1/2021 | Groth | G16H 15/00 |
| 2021/0093301 | A1* | 4/2021 | Wang | G06V 40/16 |

FOREIGN PATENT DOCUMENTS

| | | |
|---|---|---|
| JP | 2008-541889 | 11/2008 |
| JP | 2015-186505 | 10/2015 |
| WO | 2006/057740 A2 | 6/2006 |
| WO | 2006/128302 A1 | 12/2006 |
| WO | 2017006933 | 1/2017 |
| WO | 2017/060791 A1 | 4/2017 |

OTHER PUBLICATIONS

Shin, S. et al., "Joint Weakly and Semi-Supervised Deep Learning for Localization and Classification of Masses in Breast Ultrasound Images", Generic Colorized Journal, Oct. 1-15, 2017.
Uniyal, N. et al., "Ultrasound RF Time Series for Classification of Breast Lesions", IEEE Transactions on Medical Imaging, 34(2): 652-661 (Feb. 2015).
Chinese Rejection Decision in Application 201980027606.5, mailed Jun. 20, 2024, with English translation, 17 pages.
Xin Weidong et al., China Ocean University Press, pp. 225-226, Aug. 31, 2015 (no English translation).
PCT International Preliminary Report on Patentability in International Application PCT/US2019/031094, mailed Nov. 19, 2020, 11 pages.

* cited by examiner

BREAST ULTRASOUND WORKFLOW APPLICATION

CROSS REFERENCE TO RELATED APPLICATIONS

This application is a National Stage Application of PCT/US2019/031094, filed May 7, 2019, which claims priority to U.S. Provisional Patent Application No. 62/668,078, filed May 7, 2018, the disclosures of which are hereby incorporated by reference herein in their entireties. To the extent appropriate, a claim of priority is made to each of the above disclosed applications.

BACKGROUND

Procedures involving the use of an ultrasound device may include initial diagnostic exams, guidance during interventional procedures, excision confirmation, post excision marker placement, pre-surgical localization procedures, and/or visualization during a surgical procedure. In a diagnostic exam, a technician or radiologist uses the ultrasound device to scan the breast to identify and visualize the existence of potentially cancerous breast lesions, cysts, or other regions or features of interest. Once detected, an interventional procedure, such as a biopsy, may be performed to excise a sample of tissue from the detected lesion or cyst to determine whether that tissue is malignant or benign. The interventional procedure may require the use of an ultrasound device to visualize and locate the detected lesion, guide the technician during the biopsy procedure, confirm that the region of interest has been accurately sampled, and place a marker for subsequent procedures. If it is determined that the sampled tissue is in fact malignant, a recommended course of action may be to remove the identified tumor in a surgical procedure. Prior to the surgical procedure, a separate pre-surgical procedure, called localization, may also include the use of an ultrasound device to locate the tumor in order to guide the surgeon during surgical removal of the tumor.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for executing an ultrasound workflow tool that facilitates procedures, such as a diagnostic exam, an interventional procedure, a localization procedure and/or a removal (excision) surgery, by anticipating procedure workflow steps and automatically providing pertinent prompts and information in real time.

In an aspect, a computer device having a processor and memory may be provided. The computing device storing computer-executable instructions that implement an ultrasound workflow tool for facilitating a diagnostic procedure. The computer-executable instructions causing the computing device to receive one or more signals from an ultrasound probe scanning an anatomical feature of a patient and detect, by the ultrasound workflow tool, a region of interest associated with the scanned anatomical feature. The computer-executable instructions further causing the computing device to cause display of the region of interest on a display of the computing device and provide a prompt for classifying the detected region of interest. In response to receiving a classification of the region of interest, the computer-executable instructions further causing the computing device to provide a template for identifying at least one location of the classified region of interest and provide a review screen comprising one or more fields for characterizing the classified region of interest. Additionally, the computing device programed to receive a description into each of the one or more fields for characterizing the classified region of interest and to generate a report of the diagnostic scan based in part on the classified region of interest, the received at least one location, and the received one or more descriptions. As should be appreciated, one or more of the described steps may be optionally performed.

In another aspect, a method for facilitating an interventional procedure is provided. The method is performed by an ultrasound workflow tool operating on a computing device having a processor operatively coupled to an ultrasound device. The method includes receiving one or more signals from an ultrasound probe scanning an anatomical feature of a patient and detecting, by the workflow tool, a lesion associated with the anatomical feature. Additionally, the method includes capturing a pre-fire image of a needle positioned at the lesion and automatically annotating the pre-fire image. The method further includes capturing a post-fire image of the needle at the lesion and automatically annotating the post-fire image. Also, the method includes generating a report of the interventional procedure based in part on the annotated pre-fire image and the annotated post-fire image. As should be appreciated, one or more of the described steps may be optionally performed.

In still another aspect, a method for facilitating a localization procedure is provide. The method is performed by an ultrasound workflow tool operating on a computing device having a processor operatively coupled to an ultrasound device. The method includes receiving one or more signals from an ultrasound probe scanning an anatomical feature of a patient and causing display of an image associated with the scanned anatomical feature on a display of the computing device. The method further includes detecting, by the workflow tool, a first position of a localization device in a region associated with the scanned anatomical feature, determining a distance between the cancerous tissue and the first position of the localization device and providing the distance. Based on detecting a movement of the localization device to a second position, the method includes recalculating the distance and providing the recalculated distance. Based on the recalculated distance between the localization device and the cancerous tissue, the method includes providing guidance for advancing the localization device toward the cancerous tissue. As should be appreciated, one or more of the described steps may be optionally performed.

In yet another aspect, a method executed by a computing device having at least a processor that implements a workflow tool for facilitating an ultrasound diagnostic procedure is provided. The method includes receiving one or more signals from an ultrasound probe scanning an anatomical feature of a patient, detecting, by the ultrasound workflow tool, a region of interest associated with the scanned anatomical feature, and causing display of the region of interest on the display. The method further includes providing a prompt for classifying the detected region of interest and receiving a classification of the region of interest. In response to receiving the classification, the method includes providing a template for identifying at least one location of the classified region of interest and providing a review screen comprising one or more fields for characterizing the classified region of interest. Additionally, the method includes receiving a description into each of the one or more fields for characterizing the classified region of interest and generating a report of the diagnostic scan based in part on the classified region of interest, the received at least one location, and the received one or more descriptions. As should be appreciated, one or more of the described steps may be optionally performed.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1A:
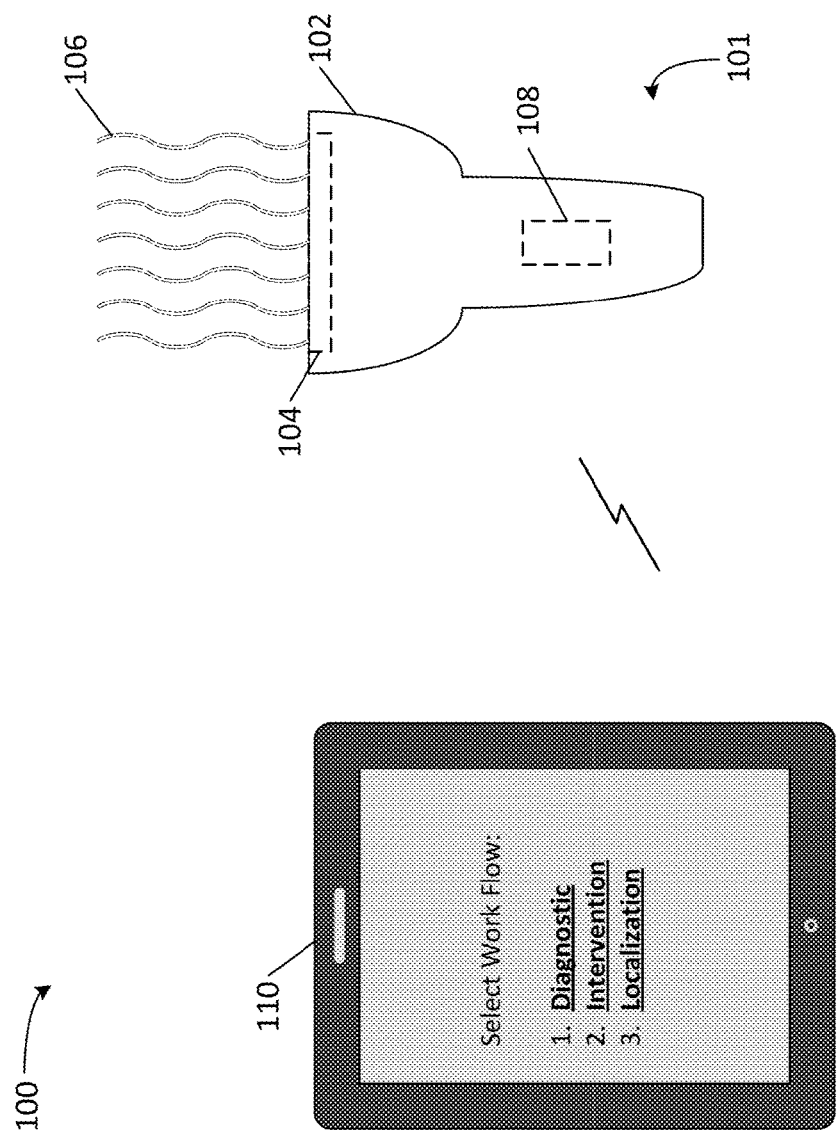
FIG. 1A depicts an example of a wireless ultrasound system.

In the following detailed description, references are made to the accompanying drawings that form a part hereof, and in which are shown by way of illustrations specific embodiments or examples. These aspects may be combined, other aspects may be optionally utilized, and structural changes may be made without departing from the present disclosure. Embodiments may be practiced as methods, systems or devices. Accordingly, embodiments may take the form of a hardware implementation, an entirely software implementation, or an implementation combining software and hardware aspects. The following detailed description is therefore not to be taken in a limiting sense, and the scope of the present disclosure is defined by the appended claims and their equivalents.

As described above, the disclosure generally relates to an ultrasound workflow tool that facilitates procedures, such as a diagnostic exam, an interventional procedure, a localization procedure and/or a removal (excision) surgery, by anticipating procedure workflow steps and automatically providing pertinent prompts and information in real time.

During a diagnostic exam, the ultrasound operator typically scans the breast and captures a number of two-dimensional images. These two-dimensional images may be annotated with minimal information associated with identified anomalies, such as indications of which anatomical feature was scanned (e.g., right or left breast), a number of anomalies identified, estimated polar (or clock) coordinates of such anomalies (e.g., with a nipple of the breast as center point), or basic tissue depth (e.g., first, second, third depth layers). Non-limiting examples of such annotations are described and illustrated with respect to FIGS. 2a-4b of U.S. Publication No. 2011/0208052 to Entrekin, and with respect to FIGS. 3-4 of Int'l Pub. No. WO2017/060791 to Roger, the limited disclosures of which are hereby incorporated herein by reference. In contrast, the present application discloses and claims an integrated workflow tool that not only anticipates each step of a procedure workflow, providing pertinent prompts, templates and information to facilitate the procedure and inform the practitioner, but may draw from information and data captured during previous procedures to further augment and facilitate a current procedure.

The scan is thereafter printed and placed in the patient's file. The radiologist or surgeon later analyzes the scan to confirm the operator's findings and may order an interventional procedure to determine whether a region of interest is cancerous. For instance, during an interventional procedure, such as an image-guided breast biopsy, potentially cancerous tissue is extracted from a targeted location of a patient for further examination. Once the needle is inserted into the patient, the location of the needle can no longer be visually identified. Accordingly, during the biopsy, the surgeon may use an ultrasound device to guide the needle to the lesion, while also capturing images during the entirety of the procedure. The surgeon will capture images as the needle is being guided to the lesion as well as capture images before the needle is fired, after the needle is fired into the lesion site, and to obtain a cross-sectional image of the lesion. However, during this procedure, the medical professional holds the ultrasound probe in one hand while guiding the needle to the lesion site with the other hand. Accordingly, capturing images and characterizing regions of interest is cumbersome and inefficient. However, these images serve as evidentiary proof of the complete performance of the procedure as well as the basis for later analysis of the lesion tissue. After completion of the intervention procedure, the medical professional later characterizes and annotates each of the images.

If a region of interest is determined to be cancerous, an excision procedure may be ordered. However, prior to the excision procedure, during an image-guided pre-surgical localization procedure, a device is placed to pin point the location of the cancerous tissue using an imaging modality. This localization procedure allows the surgeon to use the location device to remove the cancerous tissue from the patient. During the localization procedure, the medical professional will hold the ultrasound device in one hand while placing either a wire or a wireless localization device at the site of the cancerous tissue. The surgeon during the excise procedure therefore relies on the pre-implanted localization device to target the cancerous tissue by locating the localization device using imaging to guide the incision instrument to the cancer site, and to make any necessary adjustments throughout this process. Once the incision instrument is located at the cancer site, the live ultrasound image is used to make sure the entirety of the cancerous tissue and, optionally, the surrounding margins were removed.

The present application seeks to address and overcome many of the challenges of the above-described, multi-procedural set of workflows for diagnosing and treating cancerous tissues. For example, the use of ultrasound in close contact to the body of the ultrasound probe is needed in order to provide imaging. This necessitates the ultrasound transceiver to be operated with one hand while the other hand is free to operate the ultrasound interface, record images, and handle tools. This poses a unique challenge not present for other modalities, because the medical professional is limited in what he or she can do in addition to operating the ultrasound transceiver. Furthermore, the specific ultrasound-guided procedures such as the diagnostic exam, interventional procedure, and localization procedure described above each have unique challenges. Currently with the ultrasound guided diagnostic exam, only rudimentary annotations by an ultrasound technician (e.g., indications of which breast was scanned, a number of anomalies identified, estimated polar (or clock) coordinates of such anomalies, basic tissue depth layer), sometimes by hand, are captured on a printed report, leaving the radiologist or surgeon to subsequently review the report and make assessments on insufficient data and basic annotations.

The information obtained about the patient from the diagnostic exam may not be accessible for the purposes of the interventional procedure and the medical professional performing the biopsy would have to determine the location of the cancerous tissue for the purposes of targeting the correct area of the breast. In addition, during the interventional procedure, the medical professional operates the ultrasound transceiver with one hand and the biopsy device with the other, making it hard to make any notations during the procedure. With the interventional procedure, many images may need to be captured during the procedure. The medical professional typically goes back to characterize each image at a later time—oftentimes hours after the procedure, and sometimes even after multiple other procedures. The medical professional may therefore spend unnecessary additional time recalling context relating to each of the captured images, making it challenging for the medical professional to accurately recall the information pertaining to each image. Furthermore, the nature of the breast tissue of the patient affects how the medical professional operates the biopsy tool to obtain the sample of tissue, for example if the tissue is dense, whether there are calcifications, breast implants, etc. Without having access to the diagnostic exam, the medical professional has to spend unnecessary additional time understanding the nature of the breast tissue in order to perform the interventional procedure.

Similarly, during the localization procedure, which is often several weeks to months following the interventional procedure and likely conducted at a different facility with different medical staff, information obtained during the intervention procedure may not be assessable for purposes of placing the localization device. For instance, while a paper copy of the previous ultrasound images may be included in the patient's chart, as a technical matter during the localization procedure, the legacy ultrasound images and associated information may not be accessible and/or compatible for reference or side-by-side comparison with displayed images generated by the ultrasound device being used for the localization procedure. Thereafter, during the image-guided tissue excise surgery, the medical professional relies exclusively on the localization device placed prior to the procedure to locate the cancerous tissue and identify the boundaries thereof to excise a correct amount of cancerous tissue. Similar to above, the information obtained during the diagnostic exam, the interventional procedure or the localization procedure may not be accessible during the excision procedure, leaving the medical professional to spend time re-evaluating the characteristics of the tissue, the location of the lesion in addition to performing the surgery.

Embodiments described herein improve upon the prior technology by providing novel and inventive ultrasound workflow tools. The enhanced ultrasound workflow tools facilitate use of an ultrasound device during operation of a diagnostic exam, an interventional procedure, and/or a localization procedure. Not only are these workflow tools customized for each procedure, but they are integrated to provide cross-procedure information at a physician's fingertips. That is, all of the imaging and information collected via ultrasound for a particular patient across different procedures, different medical facilities, and different medical staff may be compiled and accessed during subsequent procedures via the workflow tools. Such compilation and integration of clinical and/or diagnostic information regarding patient lesion(s) enables medical professionals to make well-informed assessments and to perform procedures more precisely and efficiently, not only saving time and effort on behalf of medical personnel but potentially reducing the durations of at least some procedures—benefiting both patients and medical facilities. The workflow tools are able to anticipate the next step in a workflow of each procedure to provide prompts and/or additional information (e.g., imaging and diagnostics from previous procedures) that are pertinent to the particular step.

In one example, the ultrasound workflow tools are part of an application that is executed on a wireless computing device, and is used in connection with a wireless ultrasound device. In other examples, the ultrasound device is a wired device that is capable of communicating with the wired computing device on which the ultrasound workflow tool application operates.

With respect to a diagnostic breast exam, the ultrasound workflow tool enables the ultrasound operator to concisely characterize each lesion as it is identified during the exam. This characterizations may include, for example, the following details about the lesion: size, location (region and depth), readability, parenchymal pattern, classification as a focal lesion, margins, shape, echo pattern, orientation, posterior features, calcifications, and classification (lesion, cyst, etc.). In one example, in response to detecting a lesion, the ultrasound workflow tool may prompt the operator to describe the detected area as a lesion or a cyst and to identify the location (region and even depth) of that lesion/cyst on a pictogram. After completion of the exam, the ultrasound workflow tool may further prompt the operator to further characterize each detected lesion or cyst according to the above features using, for example, a series of check boxes and text inputs. In another example, the ultrasound workflow tool may provide the ultrasound operator with an automatically characterized description of the detected lesion, to which the operator need only confirm or edit the characterization. The operator repeats these steps until the diagnostic exam is completed.

Thereafter the ultrasound workflow tool gathers the data obtained during the exam to generate a detailed report for the patient's file. This report includes a complete characterization of each detected lesion and a pictogram of the patient's breasts that visually depict the location of each detected lesion. Accordingly, the ultrasound workflow tool enables an ultrasound operator to quickly and efficiently characterize detected lesions during or immediately following the diagnostic exam. Because this is done during or immediately following completion of the scan, the ultrasound operator does not have to rely on memory to add any characterizations to the patient's report. Furthermore, the report generated by the ultrasound workflow tool is a complete report, fully characterizing each lesion detected during the exam, and not just a mere annotation of a scan.

Any follow up diagnostic scan or another ultrasound procedure would be able to access the information, including characterization of the lesion, entered during the diagnostic exam and generated as part of the report described above. For any subsequent diagnostic scan, the next medical professional can save time by referencing the information previously entered and compiled by the workflow tool.

With respect to an interventional procedure such as an image-guided breast biopsy, the ultrasound workflow tool facilitates the procedure for the medical professional, who is also operating the ultrasound with one hand and the biopsy device in the other, by automatically capturing images as the medical professional performs the biopsy. In particular, as will be described in further detail herein, a biopsy procedure requires the medical professional to perform a sequence of steps, each of which must be carefully imaged and documented. In addition, the information entered as part of the diagnostic workflow, such as the location and characterization of the lesion, can be accessed by the workflow tool during the interventional procedure and used to locate the lesion for the purpose of the biopsy, thereby saving the medical professional time and effort in having to locate the lesion all over again.

Because many images are captured during the biopsy procedure, and the medical professional is unable to manually annotate during the procedure, without the use of the ultrasound workflow tool described herein, the medical professional must later rely on memory to identify and annotate those images. The ultrasound workflow tool therefore facilitates the procedure by initially prompting the medical professional to input information about the biopsy, such as, for example, the number of lesions to be tested, the type of needle used, and the needle gauge. Once this information is provided, the ultrasound workflow tool populates information about the needle so that images captured can be carefully related to the needle use. Thereafter, when the biopsy procedure begins, the ultrasound workflow tool automatically captures images as the medical professional performs the biopsy and automatically annotates each image. For example, the ultrasound workflow tool predicts and detects each step of the biopsy procedure and annotates each image captured with a description of that image for that particular lesion (e.g., image of initial placement of needle, needle pre-fire image, needle post-fire image, lesion cross-sectional image, etc.). Accordingly, the ultrasound workflow tool facilitates the procedure by automatically annotating many images captured during an interventional procedure. This avoids the excessive time normally taken by the medical professional to later annotate images, which oftentimes occurs hours after the procedure. This automatic annotation during the procedure also increases the accuracy of the annotations, avoiding situations in which the surgeon is required to recall the context relating to the particular procedure and each image captured, which may result in inaccurate annotations or missing information.

With respect to pre-surgical localization procedure, the ultrasound workflow tool facilitates the procedure for the medical professional who is also operating the ultrasound and localization device by providing the medical professional with step-by-step guidance of the localization device to the cancerous tissue. The localization device provides guidance during the excision surgical process to accurately excise cancerous tissue and a sufficient margin area around the cancerous tissue. As described, during the procedure, the medical professional initially locates the cancerous tissue by placing the ultrasound probe on the patient's breast to visually identify, using the ultrasound device, a previously implanted marker at the lesion site. Either a wire or wireless localization device is then placed at the site of the lesion and the marker. In some examples, a marker is not used during the interventional procedure, and the medical professional would need to visually identify the location of the lesion without the aid of the marker. Without the workflow tool, the medical professional would need to both locate and place the localization device on their own, determining the location of the lesion. With the workflow tool, significant time is saved and accuracy of determining placement is improved.

FIG. 1A depicts an example of a system 100 including an ultrasound device 101 connected to a wireless computing device 110 on which the disclosed ultrasound workflow tool operates. In some examples the ultrasound device 101 is a wireless ultrasound device and in other examples the ultrasound device is wired. The ultrasound device 101 includes an ultrasound probe 102 that includes an ultrasonic transducer 104. The ultrasonic transducer 104 is configured to emit an array of ultrasonic sound waves 106. The ultrasonic transducer 104 converts an electrical signal into ultrasonic sound waves 106. The ultrasonic transducer 104 may also be configured to detect ultrasonic sound waves, such as ultrasonic sound waves that have been reflected from internal portions of a patient. In some examples, the ultrasonic transducer 104 may incorporate a capacitive transducer and/or a piezoelectric transducer, as well as other suitable transducing technology.

The ultrasound probe 102 may also include a probe localization transceiver 108. The probe localization transceiver 108 is a transceiver that emits a signal providing localization information for the ultrasound probe 102. The probe localization transceiver 108 may include an RFID chip or device for sending and receiving information. For instance, the signal emitted by the probe localization transceiver 108 may be processed to determine the orientation or location of the ultrasound probe 102. The orientation and location of the ultrasound probe 102 may be determined or provided in three-dimensional components, such as Cartesian coordinates or spherical coordinates. The orientation and location of the ultrasound probe 102 may also be determined or provided relative to other items, such as an incision instrument, a marker, a magnetic direction, a normal to gravity, etc. With the orientation and location of the ultrasound probe 102, additional information can be generated and provided to the surgeon to facilitate guiding the surgeon to a lesion within the patient, as described further below. While the term transceiver is used herein, the term is intended to cover both transmitters, receivers, and transceivers, along with any combination thereof.

As shown, the ultrasonic transducer 104 is operatively connected to a wireless computing device 110. The wireless computing device 110 may be a part of a computing system, including processors and memory configured to produce and analyze ultrasound images. Further discussion of a suitable computing system is provided below with reference to FIG. 1D. The wireless computing device 110 is configured to display ultrasound images based on an ultrasound imaging of a patient. The ultrasound imaging performed in the ultrasound localization system 100 is primarily B-mode imaging, which results in a two-dimensional ultrasound image of a cross-section of a portion of the interior of a patient. The brightness of the pixels in the resultant image generally corresponds to amplitude or strength of the reflected ultrasound waves. Other ultrasound imaging modes may also be utilized. The wireless computing device 110 is further configured to operate the ultrasound workflow tool. As will be described in further detail herein, the ultrasound workflow tool may be used by an ultrasound operator in relation to a diagnostic exam, an interventional procedure, and an excision surgery procedure.

Figure 1B:
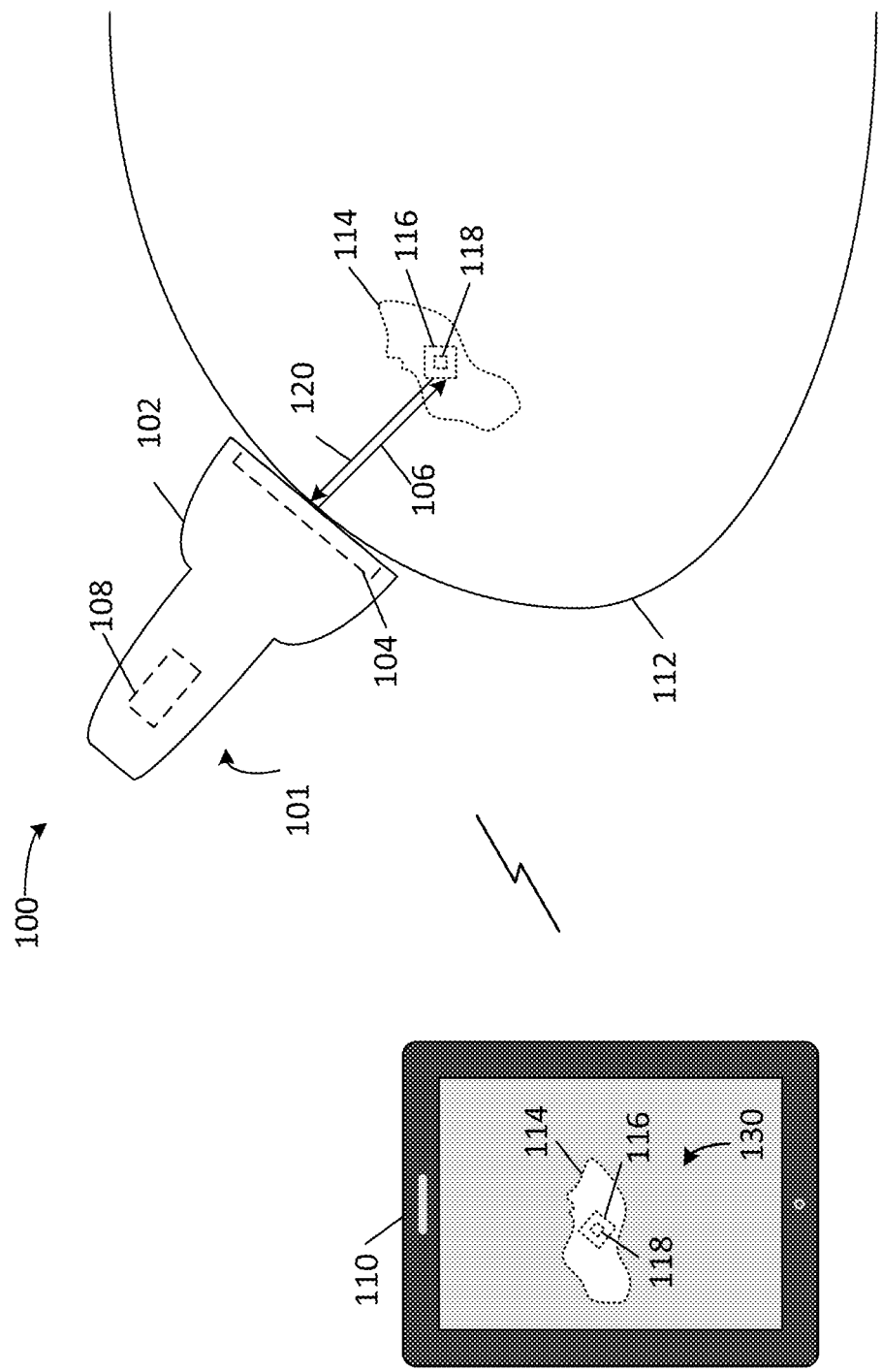
FIG. 1B depicts an example of a wireless ultrasound system used to scan a patient.

FIG. 1B depicts an example of the system 100 including a wireless ultrasound device 101 in use with a patient 112. The ultrasound probe 102 is in contact with a portion of the patient 112, such as a breast of the patient 112. In the example depicted in FIG. 1B, the ultrasound probe 102 is being used to image a portion of the patient 112 containing a lesion 114. Furthermore, in this example, a marker 116 has been implanted at the lesion 114. In aspects, the marker 116 may be implanted at the lesion during or in association with a biopsy procedure prior to the surgical procedure discussed herein. The marker 116 allows for the lesion 114 to be localized through the use of the wireless ultrasound device during a later excision surgery procedure. To image the portion of the patient 112 containing the marker 116, the ultrasonic transducer 104 emits an array of ultrasonic sound waves 106 into the interior of the patient 112. A portion of the ultrasonic sound waves 106 are reflected off internal components of the patient 112 as well as the marker 116, when the marker 116 is in the field of view, and return to the ultrasound probe 102 as reflected ultrasonic sound waves 120. The reflected ultrasonic sound waves 120 may be detected by the ultrasonic transducer 104. For instance, the ultrasonic transducer 104 receives the reflected ultrasonic sound waves 120 and converts the ultrasonic sound waves 120 into an electric signal that can be processed and analyzed to generate ultrasound image data on display 110. The depth of the marker 116 or other objects in an imaging plane may be determined from the time between a pulse of ultrasonic waves 106 being emitted from the ultrasound prove 102 and the reflected ultrasonic waves 120 being detected by the ultrasonic probe 102. For instance, the speed of sound is well-known and the effects of the speed of sound based on soft tissue are also determinable. Accordingly, based on the time of flight of the ultrasonic waves 106 (more specifically, half the time of flight), the depth of the object within an ultrasound image may be determined. Other corrections or methods for determining object depth, such as compensating for refraction and variant speed of waves through tissue, may also be implemented. Those having skill in the art will understand further details of depth measurements in medical ultrasound imaging technology.

Further illustrated is the wireless computing device 110 wirelessly connected to the wireless ultrasound device 101. In this example, the wireless computing device 110 displays an ultrasound image 130, including an image of the implanted marker 116, on the display of the wireless computing device 110. As the ultrasound probe 102 detects images, those images are simultaneously displayed on the wireless computing device 110. As will be described in further detail herein, the wireless computing device 110 executes the ultrasound workflow tool, which is operatively connected to the wireless ultrasound device 101. The ultrasound workflow tool is used to facilitate performing a diagnostic scan, an interventional procedure, and a localization and excision surgery procedure. The ultrasound workflow tool is further configured to automatically generate reports reflecting data obtained during each of the procedures.

In one example, the ultrasound workflow tool executed on the wireless computing device 110 may be used during a diagnostic breast exam. In particular, the ultrasound operator may operate the wireless ultrasound device 101 in one hand, while operating the wireless computing device 110 in the other. As the ultrasound operator scans the breast with the ultrasound probe 102, the operator may identify various areas of interest as shown on the display of the wireless computing device 110. In this example, the operator can use the ultrasound workflow tool to classify the areas of interest as a lesion or a cyst as they are detected during the diagnostic exam. The operator can also use the ultrasound workflow tool to mark, on a pictogram of the breast displayed on a display, a location indicating the region and depth of the potential lesion. This pictogram or location information can be later provided in a chart automatically generated by the ultrasound workflow tool.

In another example, the ultrasound workflow tool executed on the wireless computing device 110 may be used during an interventional procedure such as an image-guided breast biopsy. In such a procedure, the medical professional operates the wireless ultrasound device to visually guide the needle to a region of interest while also capturing images. In such a procedure, because the medical professional is operating the ultrasound probe 102 in one hand and the needle in another, the medical professional does not have the ability to annotate images during the procedure. The ultrasound workflow tool therefore is used to prompt the medical professional to advance through each step within the biopsy process, automatically capturing necessary images, and automatically annotating those images. Those annotated images can thereafter be provided in a report attached to the patient's file.

In another example, the ultrasound workflow tool executed on the wireless computing device 110 may be used during the pre-surgical localization procedure in order to place a localization device that would later be used in the excise surgery. In such a procedure, the medical professional will locate the cancerous tissue by placing the ultrasound probe on the patient's breast to visually identify a previously implanted marker at the cancer site. The ultrasound workflow tool can facilitate the procedure by providing the medical professional with updated, detailed visualization information on the display of the wireless computing device 110. Alternatively or additionally, the ultrasound workflow tool can provide step-by-step audio instructions to guide the incision tool during the excision surgery to the cancerous tissue, as well as guide the surgeon during the excising process.

Figure 1C:
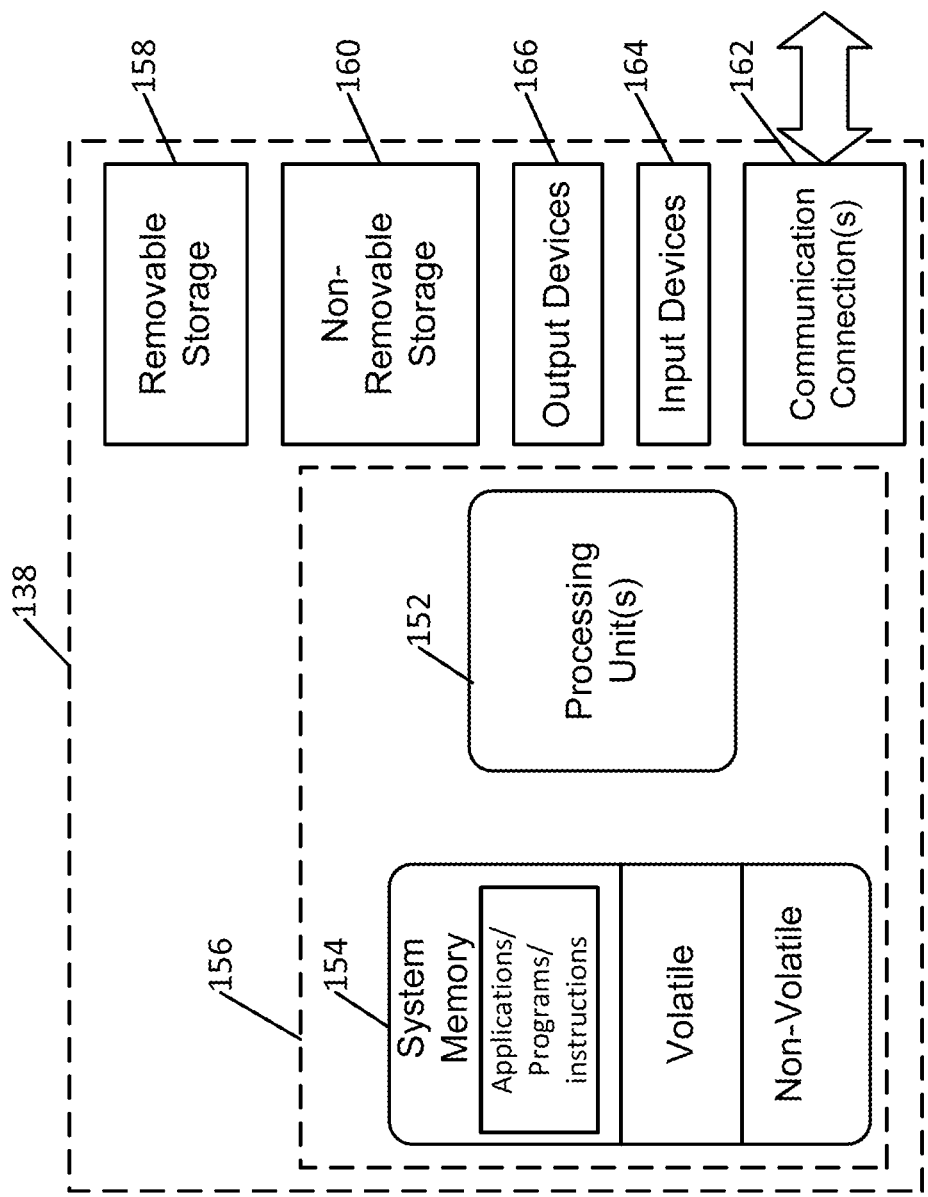
FIG. 1C depicts an example of a suitable operating environment for incorporation into the biopsy needle visualization system.

FIG. 1C depicts an example of a suitable operating environment 138 for incorporation into the disclosed system. In its most basic configuration, operating environment 150 typically includes at least one processing unit 152 and memory 154. Depending on the exact configuration and type of computing device, memory 154 (storing instructions to perform the active monitoring embodiments disclosed herein) may be volatile (such as RAM), non-volatile (such as ROM, flash memory, etc.), or some combination of the two. This most basic configuration is illustrated in FIG. 1E by dashed line 156. Further, environment 150 may also include storage devices (removable 158, and/or non-removable 160) including, but not limited to, magnetic or optical disks or tape. Similarly, environment 150 may also have input device(s) 164 such as keyboard, mouse, pen, voice input, etc. and/or output device(s) 166 such as a display, speakers, printer, etc. The input devices 164 may also include one or more antennas to detect signals emitted from the various transceivers in the system 100. Also included in the environment may be one or more communication connections 162, such as LAN, WAN, point to point, etc. In embodiments, the connections may be operable to facility point-to-point communications, connection-oriented communications, connectionless communications, etc.

Operating environment 150 typically includes at least some form of computer readable media. Computer readable media can be any available media that can be accessed by processing unit 152 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 150 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media.

Figure 2A:
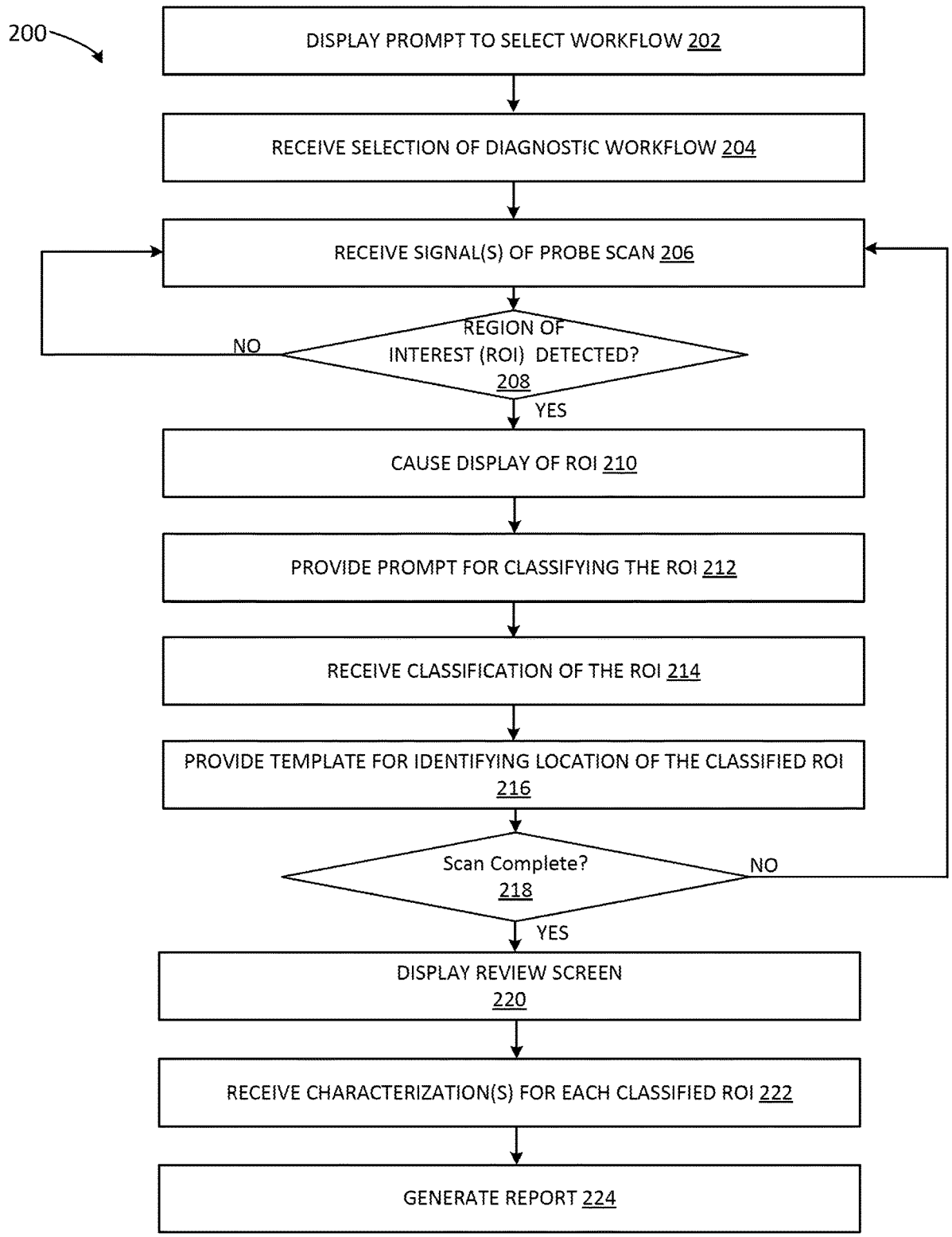
FIG. 2A depicts an example method for facilitating performing a diagnostic scan using the disclosed ultrasound workflow tool.

FIG. 2A depicts an example method 200 for facilitate performing a diagnostic scan using the disclosed ultrasound workflow tool. The method 200 may be performed by the ultrasound workflow tool executed on a wireless device having a processor such as for example the system 100 and the operating environment 150. The method 200 begins at operation 202 in which the ultrasound workflow tool displays a prompt to select a workflow from among a plurality of workflows. As described herein, the ultrasound workflow tool can facilitate various operations such as a diagnostic breast exam, an interventional procedure, a localization and/or an excision surgery. In one example, a workflow is a sequence of predetermined steps that are performed during a particular procedure. In one example, the prompt displayed is a drop down menu or some other suitable menu used to select one of a plurality of workflows associated with a procedure. In this way, regardless of the experience of a medical professional, the workflow tool anticipates a next step of the procedure and provides a suitable menu or prompt to the medical professional, thereby ensuring that the workflow tool collects appropriate information as the procedure progresses.

At operation 204, the ultrasound workflow tool receives a selection of a diagnostic workflow, related to a diagnostic breast exam. As described herein, the diagnostic breast exam procedure is a breast scan to identify any areas of interest that may be potentially cancerous. The breast scan may be performed by a medical professional using an ultrasound device having a probe that is used to scan the patient's breasts.

At operation 206, the ultrasound workflow tool receives one or more signals from the ultrasound device. In particular, in response to the medical professional performing the diagnostic scan using the ultrasound device, the ultrasound workflow tool receives one or more signals from the ultrasound device. These one or more signals may include one or more images of the patient's breast as the ultrasound device is used to scan the patient's breast during the diagnostic scan.

At operation 208, the ultrasound device is rotated around the patient's breast until a region of interest is detected. A potential region of interest may look like a darker or lighter portion on the ultrasound image. Accordingly, the ultrasound workflow tool may identify the region of interest based on a visual identification of the scan displayed on the display of the wireless computing device. In an example, the operator may select an option at the ultrasound workflow tool to indicate the region of interest.

If a region of interest is not identified (NO at operation 208) the method 200 proceeds to operation 206. If a region of interest is identified (YES at operation 208), the method 200 proceeds to operation 210 in which the ultrasound workflow tool causes display of the region of interest. In one example, this may include a zoomed in image of the region of interest.

At operation 212, the ultrasound workflow tool provides a prompt to classify the region of interest. The region of interest may be, for example, a lesion or a cyst. In some aspects, the region of interest may include more than one lesion or cyst. In this case, each lesion (or cyst) may be evaluated independently based on the operations described below, or the collection of lesions (or cysts) may be evaluated collectively based on the operations below, or some combination thereof. A lesion is an abnormal mass of tissue or swelling and a cyst is a sac that may be filled with air, fluid, or another material. In an example, the ultrasound workflow tool may display an option (e.g., a drop-down menu, a check box, or other suitable selection option) to characterize the detected region as a lesion or a cyst.

At operation 214, the ultrasound workflow tool receives the selected classification. As described, the selected classification of the region of interest may be a lesion classification or a cyst classification.

At operation 216, the ultrasound workflow tool display a template with one or more fields for characterizing the classified region of interest (e.g. a pictogram or another schematic representation of the breast). The pictogram may be, for example, a two-dimensional line diagram of the breast that enables the ultrasound operator to quickly, easily, and more accurately identify the location of the classified region of interest (e.g., lesion or cyst). In one example, the pictogram includes numerically identified circular regions that radiate from the nipple. Alternatively or additionally, a cross-sectional side view pictogram is provided, displaying alphabetical regions that radiate from the top surface of the breast to identify depth. At operation 216, the ultrasound workflow tool receives a location of the classified region of interest. In one example, the ultrasound workflow tool may receive a signal in response to the operator's selection, on the displayed pictogram, of a location of the anomaly on the pictogram. In another example, the ultrasound workflow tool may also receive a selection, from a cross-sectional pictogram view, of a depth of the anomaly. The ultrasound workflow tool may translate these one or more selections into number-letter coordinates identifying a location of the classified anomaly. Alternatively or additionally, only the location relating to the nipple is selected, thereby generating a numerical region identification of the location of the classified anomaly.

At operation 218, the ultrasound workflow tool determines whether the scan is complete. For example, a scan could be complete after the entire breast is scanned. In another example, the ultrasound operator may make a selection to end the scan. In still another example, the scan may be complete when the last lesion (or cyst) of a region of interest is characterized and, if not, may return to operation 214 to classify the next lesion (or cyst). If the scan is not complete (NO at operation 216), the method 200 proceeds to operation 206 in which the ultrasound workflow tool receives one or more signals from the ultrasound device during a continuation of the diagnostic scan of the patient's breast.

If the scan is complete (YES at operation 218), the method 200 proceeds to operation 220 in which a review screen is displayed at the ultrasound workflow tool. The review screen enables the ultrasound operator to further characterize each classified region of interest identified during the diagnostic scan. In one example, the review screen comprises a field for receiving a description corresponding to one or more parameters associated with the region of interest. The review screen may therefore prompt the ultrasound operator to provide further information regarding the following parameters for each classified region of interest: a readability finding, the parenchymal pattern (e.g., homogeneous dense, scattered density, involuted, etc.), whether it is a focal lesion, the size, margin, shape, echo pattern, orientation, posterior features, calcifications, and associated features. Although a list of features is described, it is understood that this is an exemplary list of features and that more or fewer features may be used to describe the classified region of interest.

At operation 222, the ultrasound workflow tool receives the characterizations of each classified region of interest. In an example, the features listed above are displayed as check boxes or as drop-down menu options that allow the ultrasound operator to quickly and efficiently characterize each classified region of interest identified during the scan. Furthermore, text box inputs may be provided that allow the operator to provide further description such as, for example, indications, mammography correlations, clinical correlations, impressions, and recommendations. In other examples, the ultrasound workflow tool automatically processes each classified region of interest and automatically populates the findings. Accordingly, in such an example, the ultrasound operator need only confirm, deny, or edit such findings.

At operation 224, the ultrasound workflow tool generates a report. In particular, the ultrasound workflow tool collects all the images captured during the scan, the classifications, the identified location information, the characterizations, and any comments into a report that is attached to the patient's file. The report can further include the pictogram showing a pictorial location of each detected lesion or cyst.

Although the method 200 discloses a particular sequence of operations, it is understood that these operations are exemplary, and therefore one or more of these operations may be optional or performed in a different sequence.

Figure 2B:
FIGS. 2B-2L depict example screenshots of facilitating a diagnostic scan and the generated report.

FIG. 2B depicts an example user interface 250 of the ultrasound workflow tool displaying an image of a breast as scanned by the wireless ultrasound probe. As described herein, the ultrasound workflow tool can be used to perform a diagnostic exam during which the ultrasound operator can view an image of the breast during a breast scan.

Figure 2C:

FIG. 2C illustrates an example user interface 252 of the ultrasound workflow tool displaying a lesion as detected on the ultrasound image during a diagnostic exam. In this example, the ultrasound workflow tool displays a classification user interface 254, which enables the ultrasound operator to quickly classify the region of interest as a lesion or a cyst, and to mark the boundaries of the identified region (e.g., height, width, length).

Figure 2D:

FIG. 2D illustrates an example user interface 256 of the ultrasound workflow tool displaying a lesion as marked by the ultrasound operator. As shown, the ultrasound workflow tool enables the ultrasound operator to quickly and accurately mark the boundaries of the classified region of interest (e.g., lesion or cyst). In this example, the marking further corresponds to a size of the classified region of interest, as shown on the user interface 256. This user interface 256 illustrates an example in which the ultrasound operator marked both the height and length of the classified region of interest.

Figure 2E:
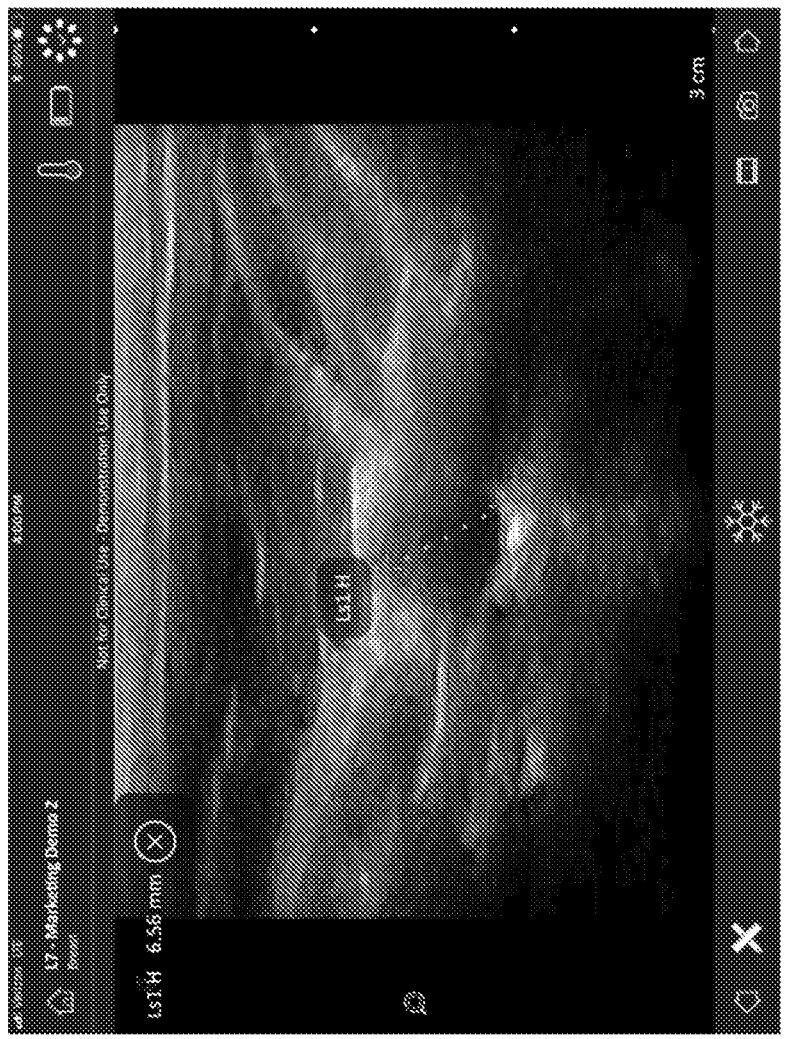

FIG. 2E depicts an example user interface 258 of the ultrasound workflow tool displaying a region of interest as marked by the ultrasound operator. This user interface illustrates an example in which the ultrasound operator marked only the height of the region of interest. This marking corresponds to a height size of the region of interest, as shown on the user interface 258.

Figure 2F:
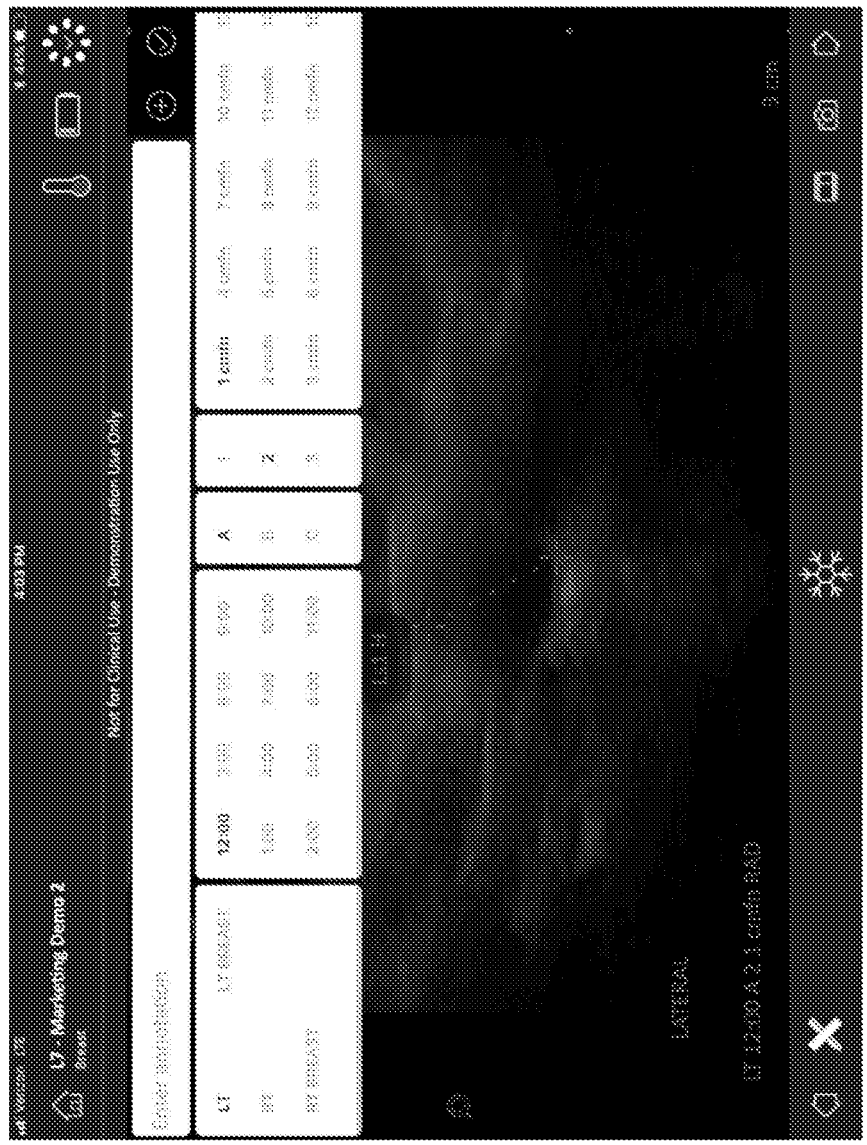

FIG. 2F illustrates an example annotation user interface 260 of the ultrasound workflow tool. The annotation user interface 260 allows the ultrasound operator to indicate, for example, the breast and a region in which the classified region of interest was found. The ultrasound workflow tool may allow the ultrasound operator to indicate a region in which the classified region of interest is located for example, by indicating an orientation from the nipple (e.g., 12:00, 1:00, 2:00 . . . ) and a depth of the classified region of interest. These may be translated into letter-number coordinates specifically pinpointing the classified region of interest.

Figure 2G:
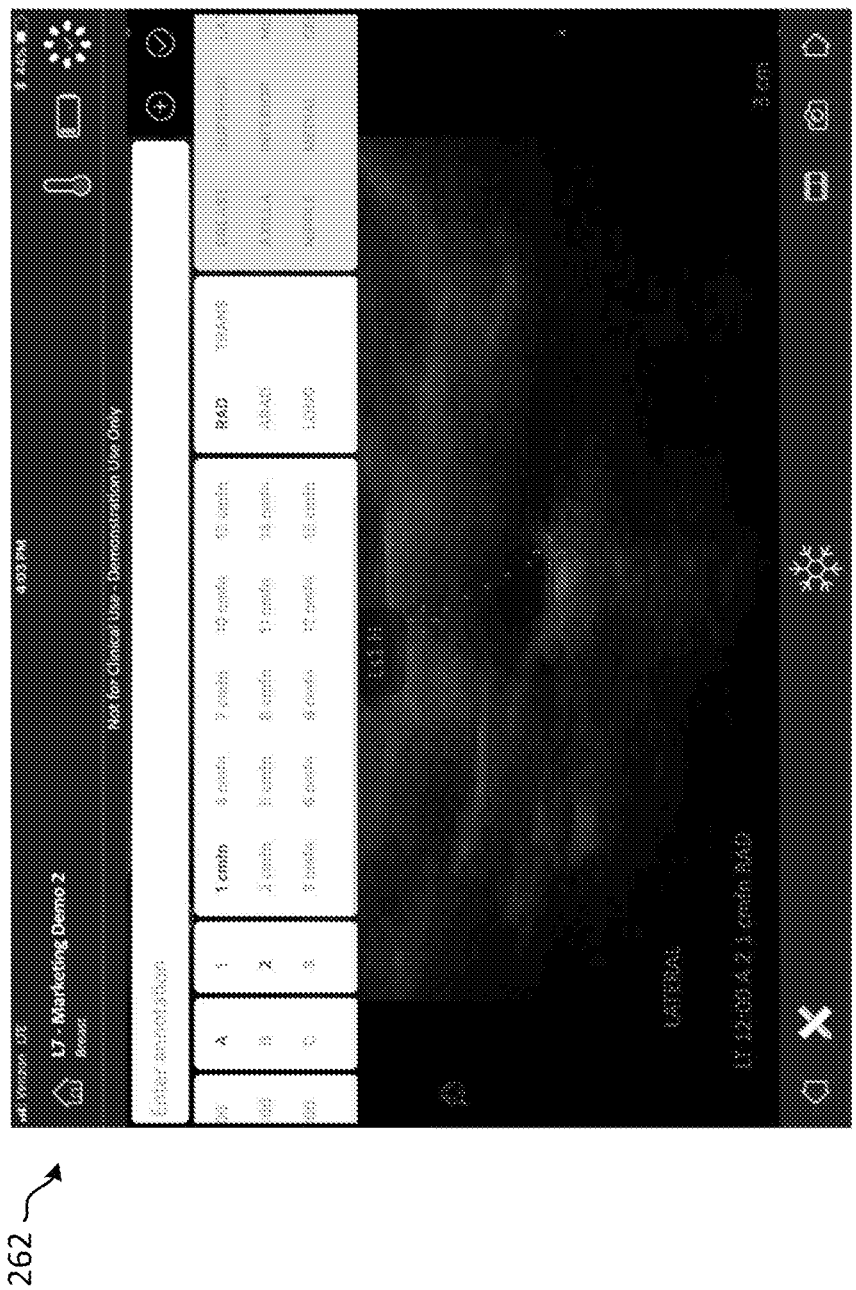

FIG. 2G depicts an example extended view 262 of the annotation user interface of the ultrasound workflow tool. This extended view 262 shows the various options in which the ultrasound operator can use to select the type, orientation, and region of the classified region of interest.

Figure 2H:
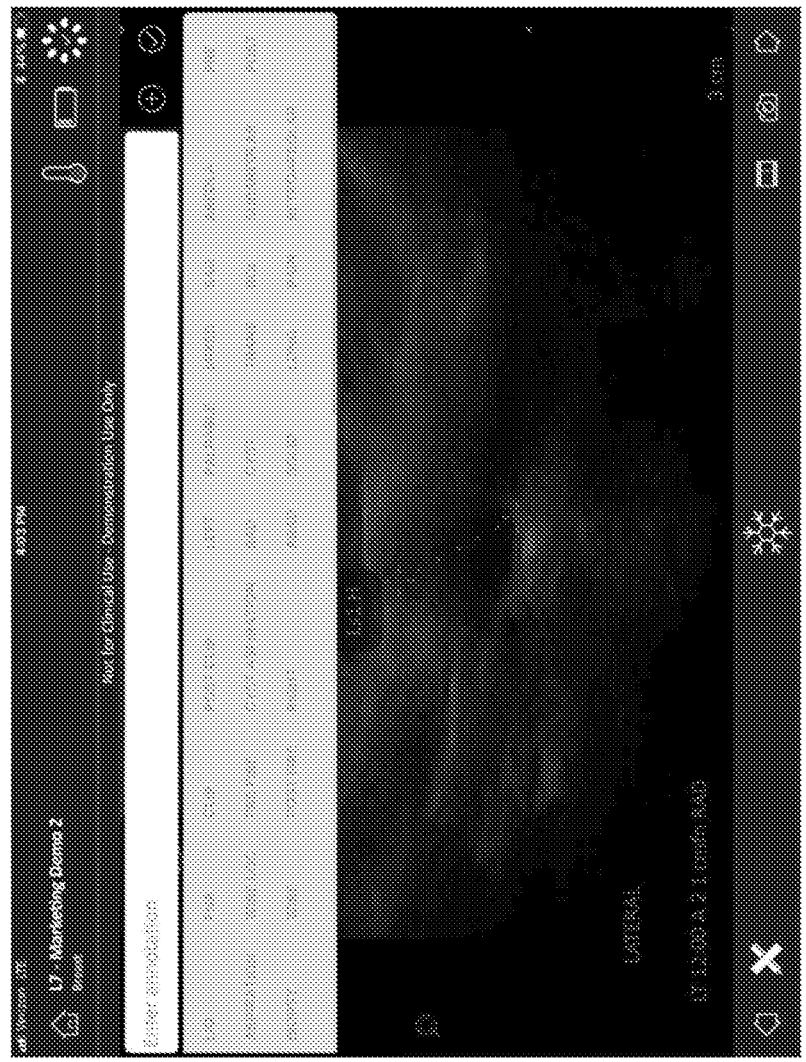

FIG. 2H illustrates an example second annotation user interface 264 of the ultrasound workflow tool. This second annotation user interface 264 enables the ultrasound operator to further indicate the type of diagnostic exam the operator is performing.

Figure 2I:
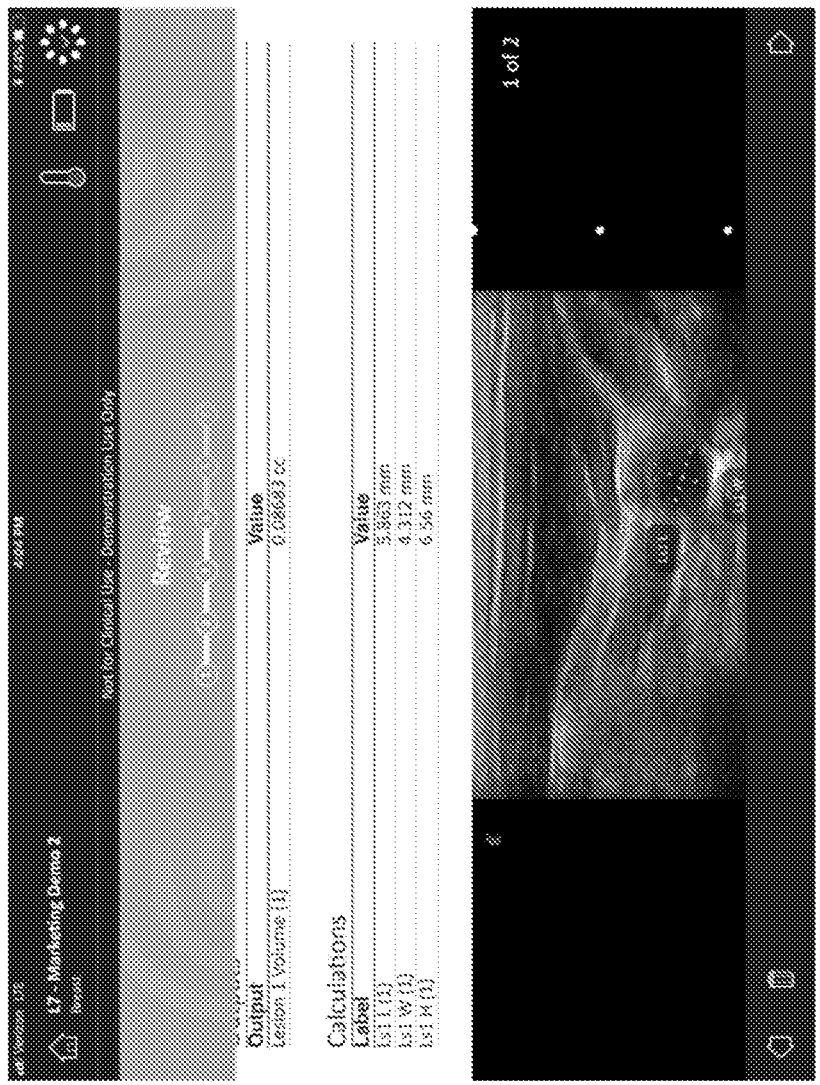

FIG. 2I illustrates an example review screen 266 of the ultrasound workflow tool. In an example, the review screen 266 is displayed as part of the application operating on the wireless computing device after completion of the diagnostic exam and provides a summary of the findings during the diagnostic exam. For example, the review screen provides a summary of each classified region of interest identified, the location of each classified region of interest, the size of each classified region of interest, and the orientation of each classified region of interest. The review screen 266 may further display calculations automatically performed based on the operator's performance of the diagnostic exam, including for example, classification of regions of interest, volume, depth-to-width ratio, among others.

Figure 2J:
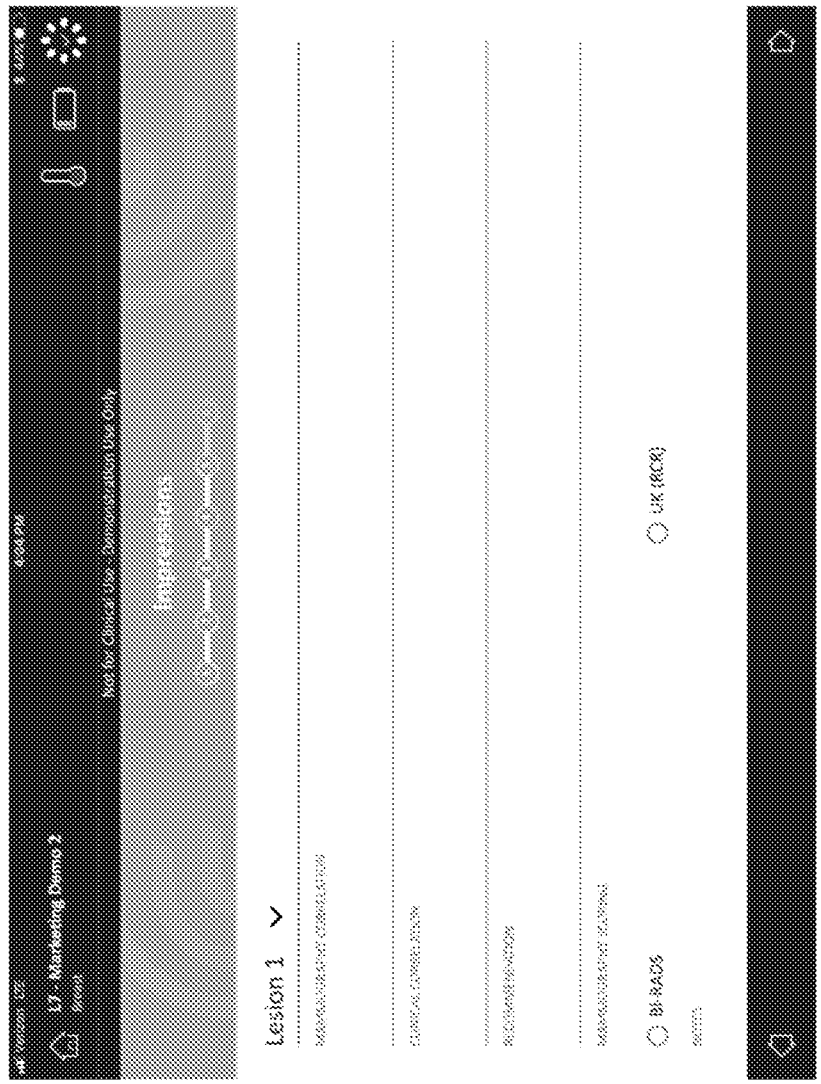

FIG. 2J illustrates an example user interface of the ultrasound workflow tool displaying another review screen 268 in which impressions can be captured. Information from other prior diagnostic exams and/or reports can be auto populated into these fields or entered from medical records associated with the patient.

Figure 2K:
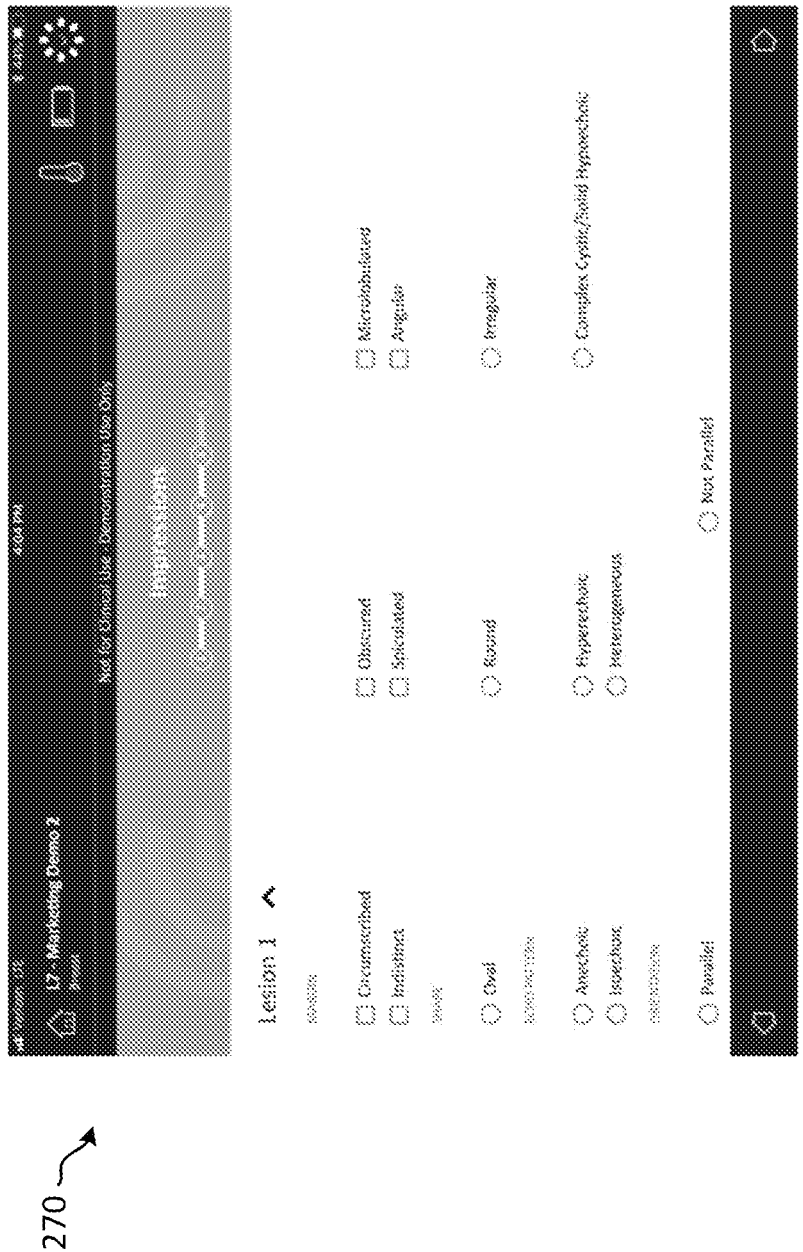

FIG. 2K illustrates an example characterization review screen 270 of the ultrasound workflow tool. The ultrasound operator can characterize each classified region of interest at the characterization review screen 270. For example, the ultrasound operator can indicate the margins of the classified region of interest, shape, echo pattern, and orientation. Although a specific set of characteristics are shown, it is understood that more or fewer characteristics may be displayed as contemplated by the disclosed ultrasound workflow tool.

Figure 2L:
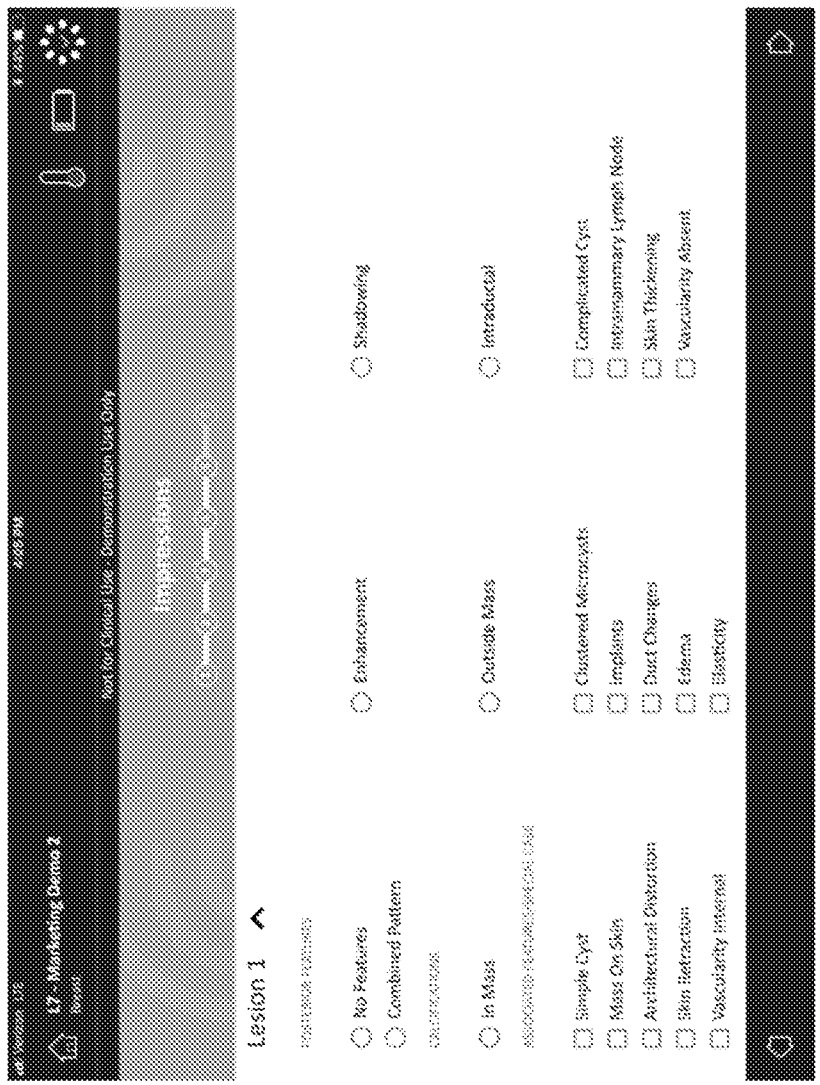

FIG. 2L depicts an example extended view of the characterization review screen 272 displayed on the ultrasound workflow tool. In this example, the ultrasound operator indicate any posterior features, calcifications, and associated features.

Figure 3A:
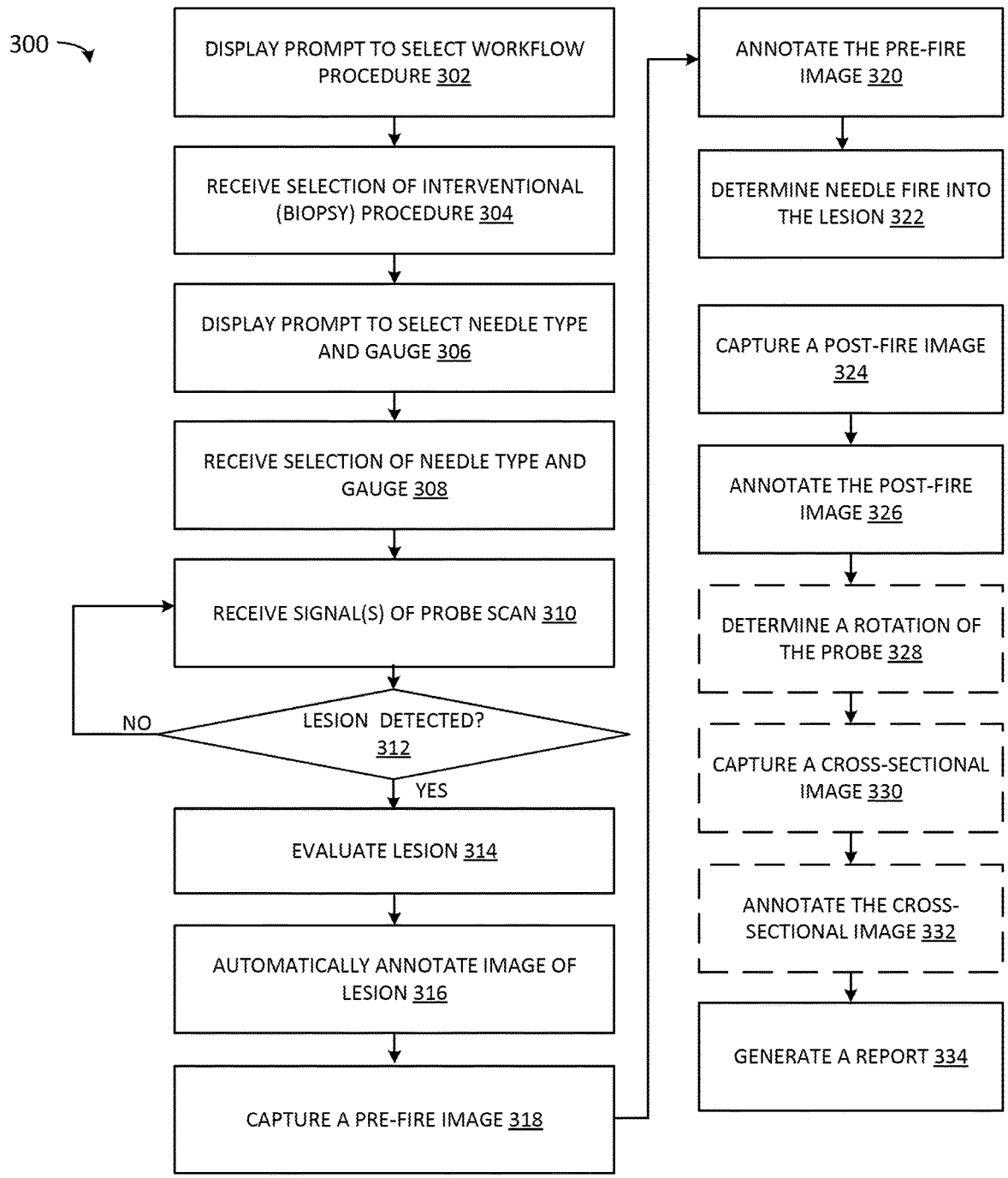
FIG. 3A depicts an example method for facilitating an interventional procedure using the disclosed ultrasound workflow tool.
Figure 4:
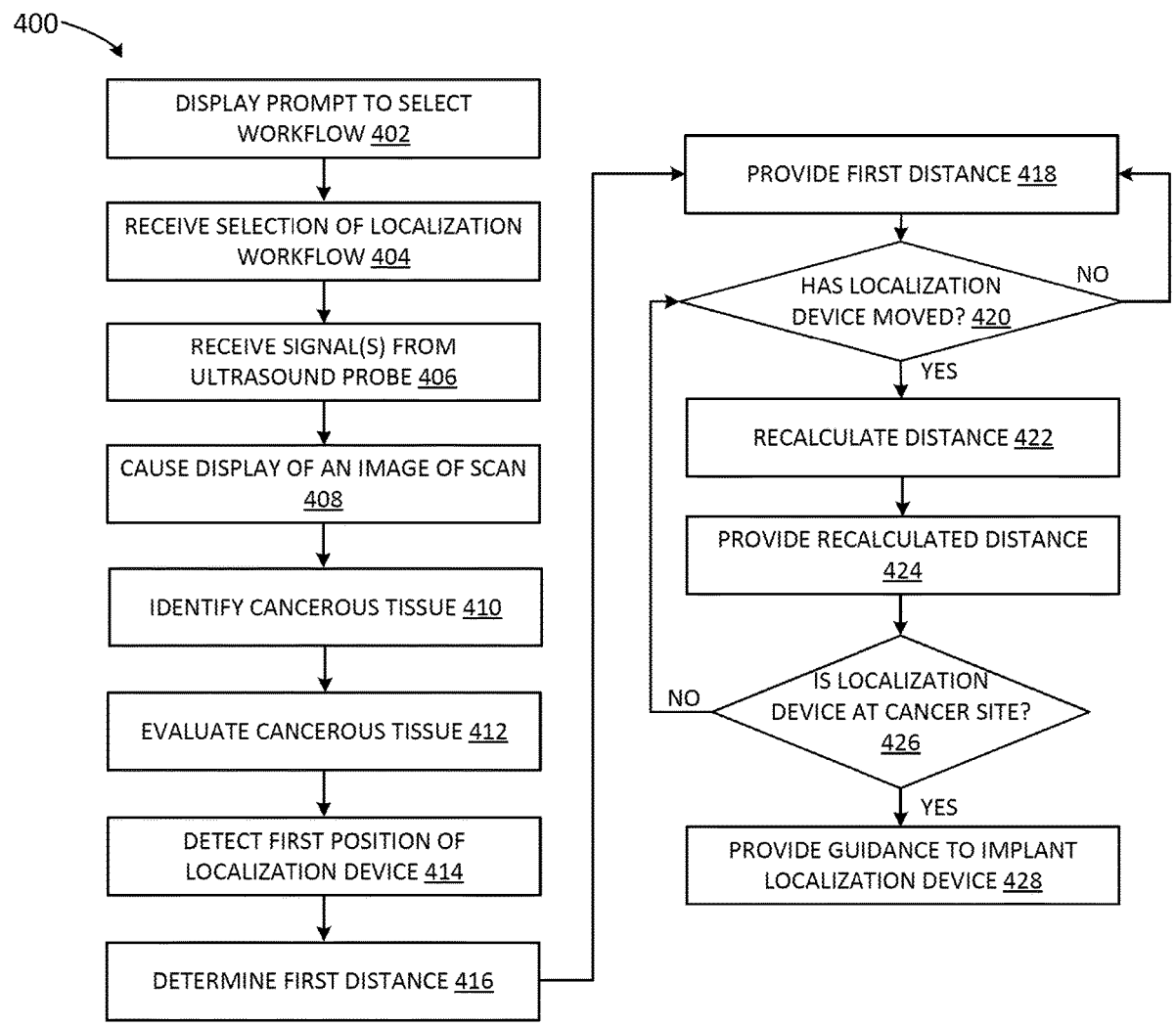
FIG. 4 depicts an example method for facilitating a localization and an excision surgery procedure using the disclosed ultrasound workflow tool.

FIG. 3A depicts an example method 300 for facilitating performing an interventional procedure using the disclosed ultrasound workflow tool. The method 300 may be performed by the ultrasound workflow tool executing on a wireless device having a processor, such as for example the system 100 and the operating environment 150. The method 300 begins at operation 302 in which the ultrasound workflow tool displays a prompt to select a workflow from among a plurality of workflows. As described herein, the ultrasound workflow tool can assist an ultrasound operator in various operations such as a diagnostic breast exam, an interventional procedure, a localization procedure, and/or excision surgery. In one example, a workflow is a sequence of predetermined steps that are performed during a particular procedure. In one example, the prompt displayed is a drop down menu or some other suitable menu used to select one of a plurality of workflows associated with a procedure.

In operation 304, the ultrasound workflow tool receives a selection of an interventional workflow procedure, such as a biopsy exam. A breast biopsy is a procedure performed to excise a sample of potentially cancerous tissue from a detected lesion or cyst to determine whether that tissue is malignant or benign. Accordingly, a biopsy may be performed sometime after a diagnostic breast exam, for example. Although this example may refer to the potentially cancerous tissue as a lesion, it is understood that this method 300 may also be used during a biopsy of a cyst.

At operation 306, the ultrasound workflow tool displays a prompt asking the ultrasound surgeon select the needle type and needle gauge used during the biopsy procedure. As described herein, during the image-guided breast biopsy, potentially cancerous tissue is extracted from a targeted location of a patient using a needle. Once the needle is inserted into the patient, the location of the needle can no longer be visually identified. Accordingly, during the biopsy, the surgeon uses an ultrasound device to guide the needle to the lesion, while also capturing images during the entirety of the procedure. Understanding the needle type and gauge is important because different needles have different sizes, and some are spring-loaded or have other "firing" mechanisms that cause a portion of the biopsy needle to extend to capture a sample of the lesion tissue. Accordingly, at operation 306, the ultrasound workflow tool may display a prompt asking the surgeon or other person to select the type and gauge of the needle from among a plurality of optional needle types and sizes. In an example, the prompt provides a drop-down menu, a selection box, or other suitable selection feature to select the appropriate needle and type.

At operation 308, the ultrasound workflow tool receives a selection of the needle type and gauge. In an example, a selection is received in response to the surgeon's selection at the prompt displayed at operation 306. In response thereto, the ultrasound workflow tool may populate needle and gauge information. This information may be used during the biopsy operation (e.g., in order to detect various steps within the procedure). In some aspects, operation 308 may be optional and the method may advance from operation 306 to operation 310.

At operation 310, the ultrasound workflow tool receives one or more signals from the ultrasound device. In particular, during the interventional procedure, the medical professional starts scanning the patient's breast using the ultrasound device. Accordingly, the ultrasound workflow tool receives one or more signals, which may include one or more images of the patient's breast as the ultrasound device is used to scan the patient's breast during the interventional procedure.

At operation 312, the ultrasound workflow tool determines if a lesion is identified. In some examples, a lesion is identified by the ultrasound workflow tool based on one or more images received from the ultrasound device during a scan of the patient's breast. A lesion may look like a darker or lighter portion on the ultrasound image. Accordingly, the ultrasound workflow tool may identify the lesion based on a visual identification of the scan displayed on the display of the wireless computing device. In one example, the ultrasound workflow tool determines that a lesion is identified using the ultrasound probe based on the surgeon's indication that the lesion is found by scanning the patient's breast using the ultrasound device. Alternatively or additionally, the ultrasound workflow tool may use image analysis or machine-learning techniques to automatically identify the lesion as the surgeon scans the patient's breast and uses that understanding to automatically capture the image. In another example, the information from the diagnostic scan, such as the scan performed in steps described in reference to FIG. 2A, may be used to suggest an area where the lesion is located. This determination can be confirmed by the surgeon performing the interventional procedure. In an example, the surgeon may select an option at the ultrasound workflow tool when a lesion is identified. One or more images may be captured of the identified lesion. If a lesion is not identified (NO at operation 312), the method 300 returns to operation 310 and the surgeon continues to scan the patient's breast. If a lesion is identified (YES at operation 312), the method proceeds to operation 314.

At operation 314, the ultrasound workflow tool evaluates the lesion to determine whether the lesion was previously characterized. As described herein, the interventional procedure may be performed sometime after one or more potentially cancerous lesions are identified in a diagnostic exam. Accordingly, in operation 314, the ultrasound workflow tool determines whether the lesion identified in the scan at operation 312 is a lesion that was previously characterized during a diagnostic exam. In some examples, the lesion was not previously characterized, in which case the lesion may be a newly developed lesion or a lesion not identified during a diagnostic scan. Alternatively, the lesion identified in operation 312 may have been previously identified and characterized in a diagnostic exam. In some examples, the ultrasound workflow tool evaluates the size, location, shape, etc. of the identified lesion to make this determination.

At operation 316, the ultrasound workflow tool automatically annotates one or more images captured of the characterized lesion. In an example, the annotation may include a description of the image (e.g., initial image of the lesion), a description or identification of the particular lesion (e.g., as being a previously characterized lesion or a new lesion), a timestamp indicating the time at which the image was captured, the name of the surgeon performing the procedure, the patient's name, etc.

At operation 318, the ultrasound workflow tool captures an image of the needle before the needle is fired into the potentially cancerous lesion. In one example, the ultrasound workflow tool may receive an indication that the needle is positioned at the lesion. In one example, the ultrasound workflow tool makes this determination based on the surgeon's indication, using the ultrasound device or a foot pedal or other device operatively connected to one or more of the ultrasound device and the ultrasound workflow tool that the needle has advanced to the lesion site. Alternatively or additionally, in one example, the ultrasound workflow tool may receive an indication based on a signal received from the RFID transmitter in the needle. Alternatively or additionally, the ultrasound workflow tool may use image analysis or machine-learning techniques to automatically identify the location of the needle as the surgeon scans the patient's breast and advances the needle to the appropriate position and use that understanding to automatically capture the image. As described herein, some biopsy needles are spring-loaded or have other "firing" mechanisms that cause a portion of the biopsy needle to extend to capture a sample of the lesion tissue. Accordingly, at operation 318, the ultrasound workflow tool captures an image of the needle before the needle is fired into the potentially cancerous lesion.

At operation 320, the ultrasound workflow tool automatically annotates the one or more pre-fire images captured. In an example, the annotation may include a description of the image (e.g., pre-fire image of the needle positioned at or near the lesion site), a description or identification of the particular lesion (e.g., as being a previously characterized lesion or a new lesion), the needle type and gauge, orientation of the needle aperture, a timestamp indicating the time at which the image was captured, the name of the surgeon performing the procedure, the patient's name, etc.

At operation 322, the ultrasound workflow tool determines that the needle fired into the lesion. In one example, the ultrasound workflow tool makes this determination based on the surgeon's indication, using the ultrasound device or other device operatively connected to the ultrasound device or workflow tool, that the needle has been fired into the lesion site. Alternatively or additionally, this determination is made based on a signal received from the RFID transmitter in the needle. Alternatively or additionally, the ultrasound workflow tool may use image analysis or machine-learning techniques to automatically identify when the needle has fired into the lesion. As described herein, some biopsy needles are spring-loaded or have other "firing" mechanisms that cause a portion of the biopsy needle to extend to capture a sample of the lesion tissue. Accordingly, in operation 322, the ultrasound workflow tool may receive an indication that the needle is in a post-fire position.

At operation 324, the ultrasound workflow tool captures a post-fire image of the needle at the lesion site. The post-fire image may include an image of a portion of the needle fired into the lesion. As described herein with reference to operation 322, the ultrasound workflow tool determines that the needle is in a post-fire position and uses that understanding to automatically capture the image. Accordingly, at operation 324 one or more post-fire images are captured.

At operation 326, the ultrasound workflow tool annotates the one or more post-fire images captured. In an example, the annotation may include a description of the image (e.g., post-fire image of the needle fired into the lesion site), a description or identification of the particular lesion (e.g., as being a previously characterized lesion or a new lesion), the needle type and gauge, orientation of the needle aperture, a timestamp indicating the time at which the image was captured, the name of the surgeon performing the procedure, the patient's name, etc.

At optional operation 328, the ultrasound workflow tool determines that the ultrasound probe has rotated. The detection of a rotation of the ultrasound probe is important in order to capture a cross-sectional view of the particular lesion. In one example, the ultrasound workflow tool makes this determination based on the surgeon's indication, using the ultrasound device, that the ultrasound probe has been rotated such that a cross-sectional view of the lesion is now in focus. Alternatively or additionally, the ultrasound workflow tool may use image analysis to automatically identify when the ultrasound probe has rotated and focused on a cross-sectional view of the lesion. Alternatively or additionally, the ultrasound workflow tool may make this determination based on a signal received from ultrasound probe.

At optional operation 330, the ultrasound workflow tool captures a cross-sectional image of the lesion. The cross-sectional image may include an image of the needle fired into the lesion. Alternatively or additionally, the cross-sectional image may include an image of the needle retracted from the lesion site. In one example, the ultrasound workflow tool determines that the probe has rotated based on the surgeon's indication or based on a signal received from ultrasound probe, such as by an indication from an internal accelerometer within the ultrasound probe. Alternatively or additionally, the ultrasound workflow tool may use image analysis or machine-learning techniques to automatically identify the rotation of the probe and uses that understanding to automatically capture the image. Accordingly, at operation 330 one or more cross-sectional images of the lesion are captured.

At optional operation 332, the ultrasound workflow tool annotates the one or more cross-sectional images captured. In an example, the annotation may include a description of the image (e.g., cross-sectional image of the lesion), a description or identification of the particular lesion (e.g., as being a previously characterized lesion or a new lesion), a timestamp indicating the time at which the image was captured, the name of the surgeon performing the procedure, the patient's name, etc.

At operation 334, the ultrasound workflow tool generates a report. In particular, the ultrasound workflow tool collects the needle information provided before the interventional procedure, the images captured during the procedure, and the associated annotations. All such information is compiled into a report that is attached to the patient's file. Accordingly, the method 300 provides a quick, accurate, and efficient solution to annotating and workflow images captured during an interventional procedure, eliminating or minimizing the time it would take the surgeon to prepare the report hours after the procedure.

Although the method 300 discloses a particular sequence of operations, it is understood that these operations are exemplary, and therefore one or more of these operations may be optional or performed in a different sequence.

Figure 3B:
FIGS. 3B-3I depict example screenshots of the resulting report generated and annotated images.

FIG. 3B illustrates an example user interface 350 of the ultrasound workflow tool displaying an image of a breast as scanned by the wireless ultrasound probe. As described herein, the ultrasound workflow tool can be used to perform an interventional procedure during which an ultrasound operator (e.g., a surgeon) can view an image of the breast during an interventional procedure.

Figure 3C:
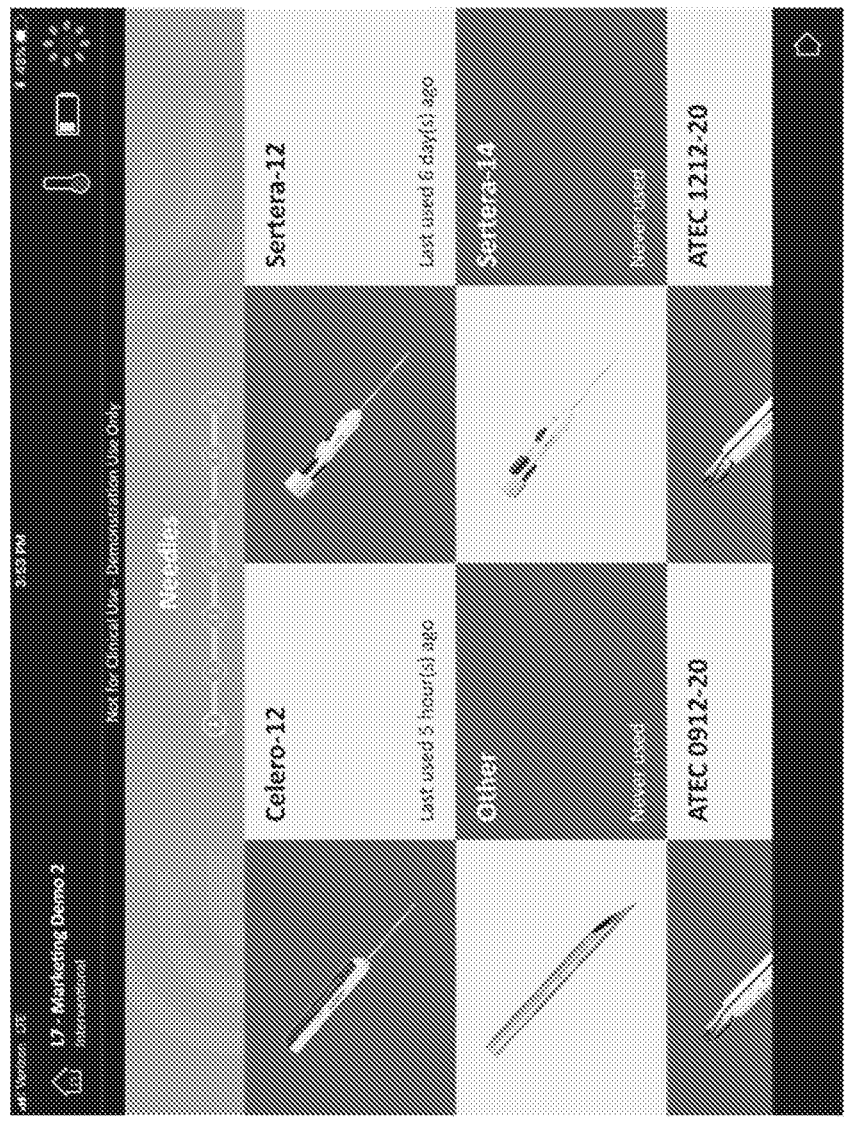

FIG. 3C illustrates an example user interface of the ultrasound workflow tool displaying a needle selection screen 352. The needle selection screen 352 enables the ultrasound operator can select the particular needle that will be used during the interventional procedure.

Figure 3D:
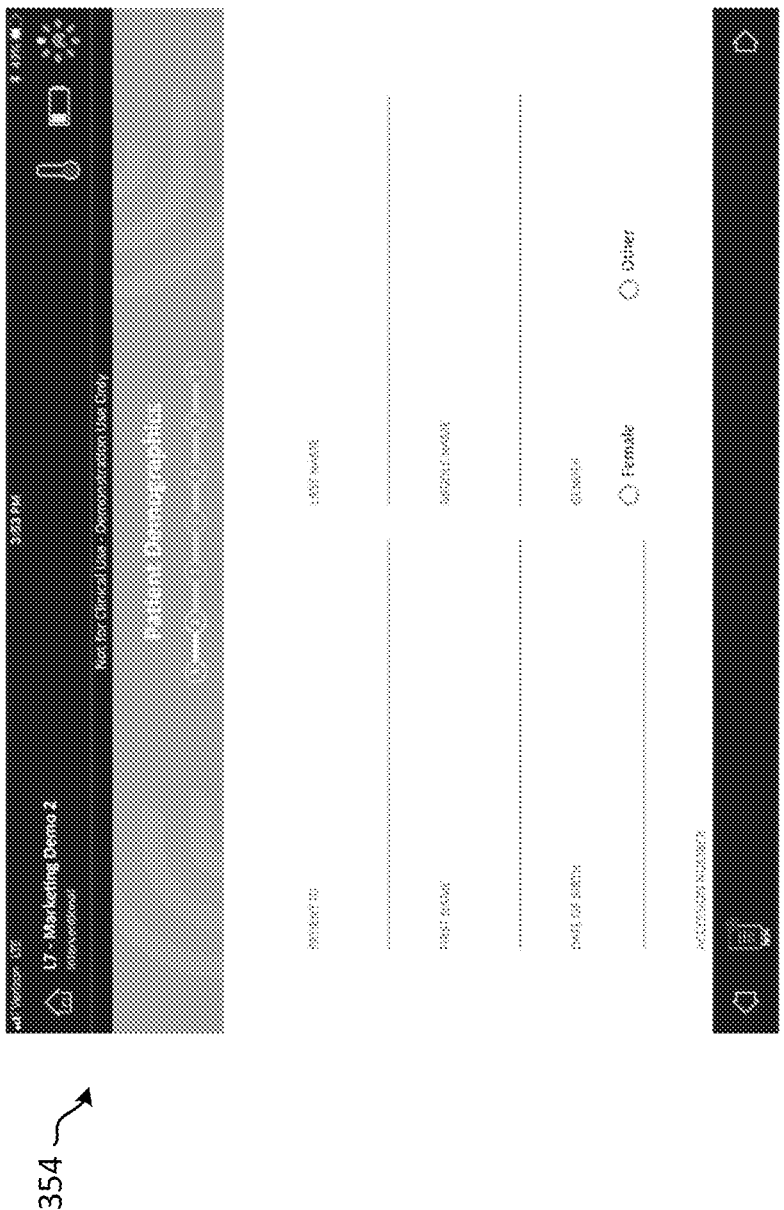

FIG. 3D illustrates an example user interface of the ultrasound workflow tool displaying a patient demographics screen 354. The patient demographics screen 354 enables the ultrasound operator to provide patient information in advance of the interventional procedure.

Figure 3E:
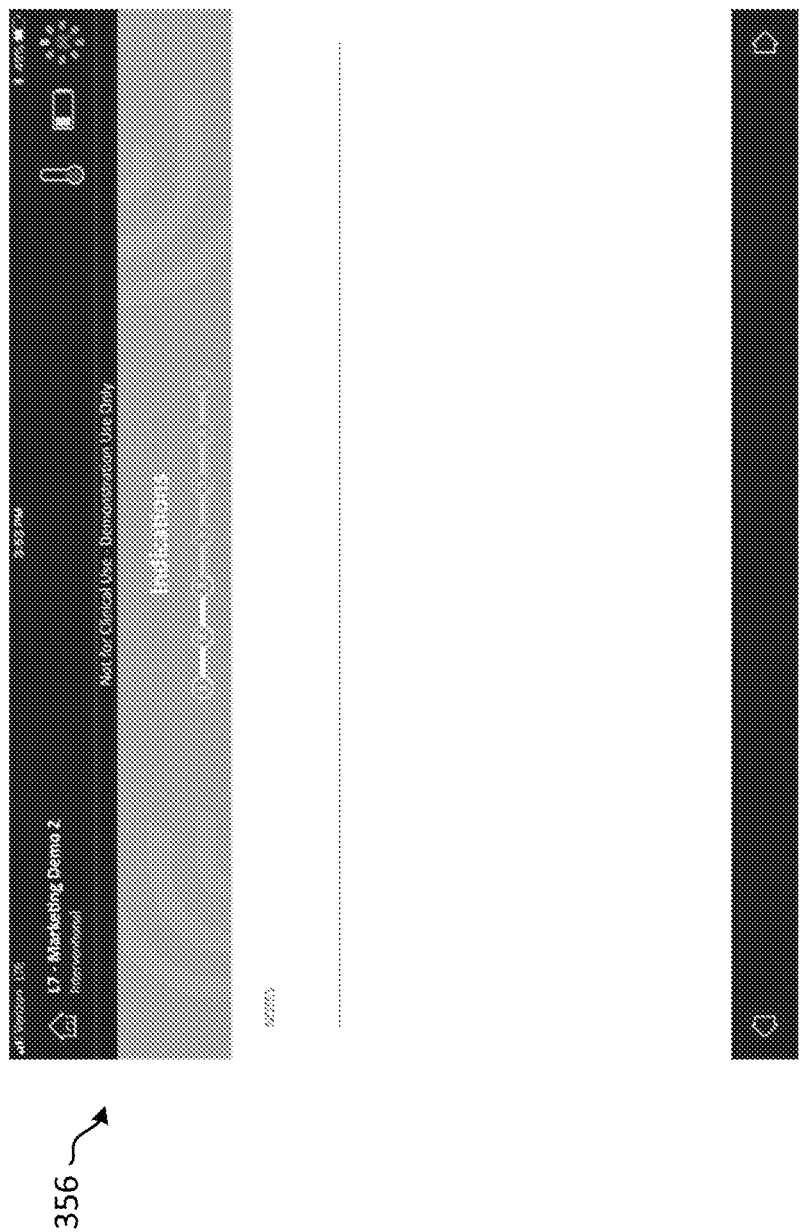

FIG. 3E illustrates an example user interface of the ultrasound workflow tool displaying an indications user interface 356. The indications user interface 356 enables the ultrasound operator to provide any notes in advance of the interventional procedure.

Figure 3F:

FIG. 3F illustrates an example user interface 358 of the ultrasound workflow tool displaying an initial image of the breast. The initial image may be taken automatically by the ultrasound workflow tool, in response to automatically detecting the lesion. As described herein, the ultrasound operator will capture images as the needle is being guided to the lesion as well as capture images before the needle is fired, after the needle is fired into the lesion site, and to obtain a cross-sectional image of the lesion. In one example, these multiple images are captured during the procedure to serve as evidentiary proof of the complete performance of the procedure as well as later analysis of the lesion tissue. Accordingly, an initial image of the breast may be captured and displayed.

Figure 3G:
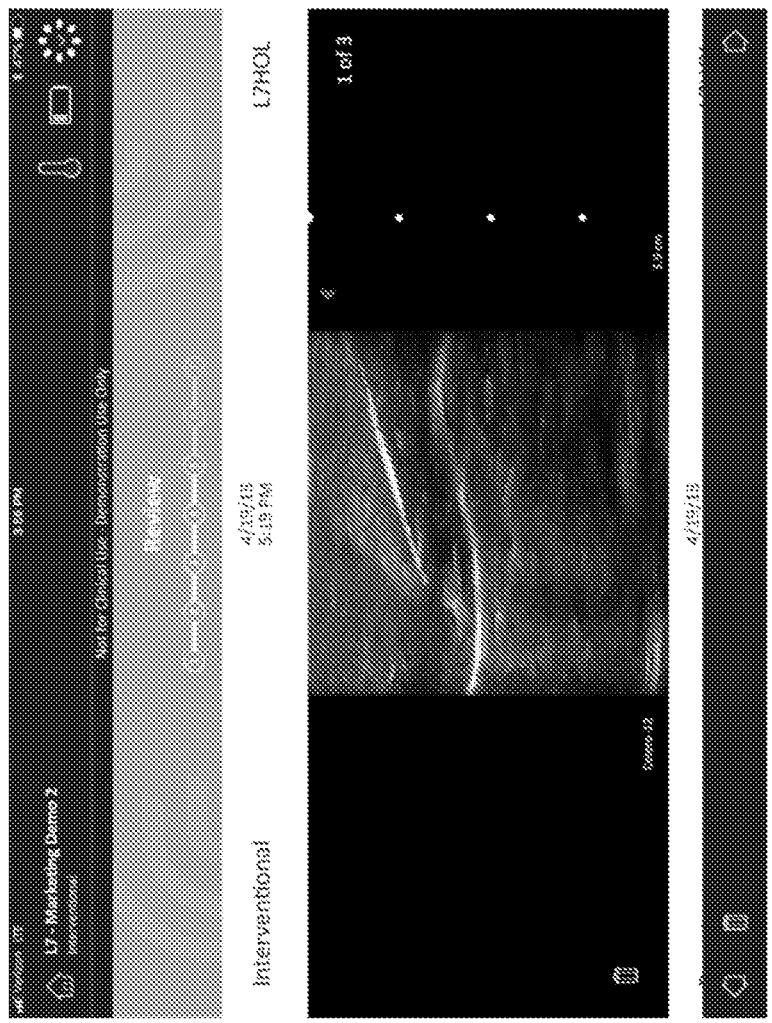

FIG. 3G illustrates an example user interface 360 of the ultrasound workflow tool displaying an image of the breast as the needle is guided to the lesion cite. As described, this image may be automatically captured in response to detection, by the ultrasound workflow tool, of the needle and the lesion.

Figure 3H:
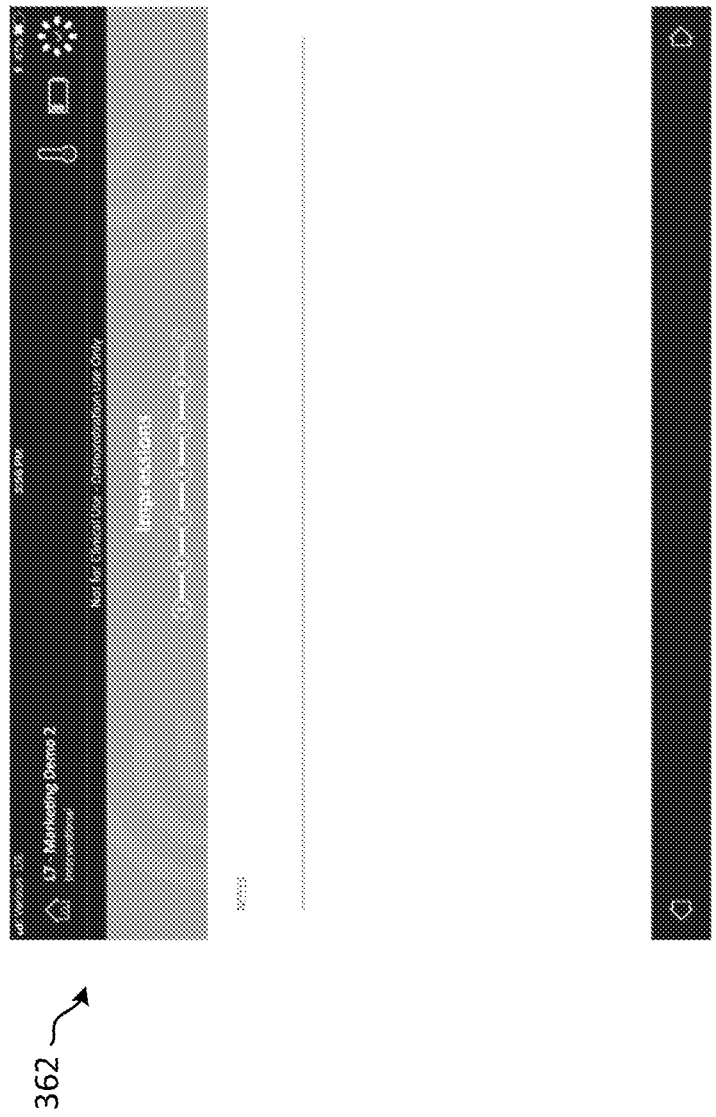

FIG. 3H illustrates an example user interface of the ultrasound workflow tool displaying a review screen 362 in which impressions can be captured. This review screen 362 may be displayed after completion of the interventional procedure.

Figure 3I:
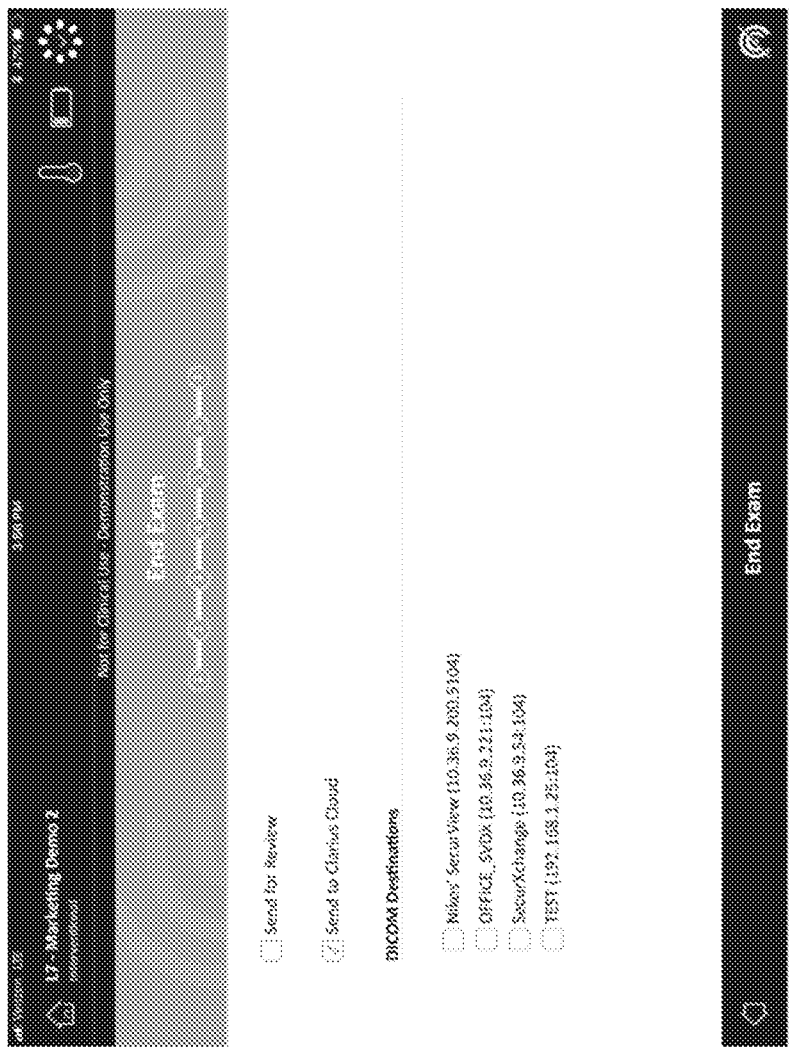

FIG. 3I illustrates an example user interface of the ultrasound workflow tool displaying an end screen 364. The end screen may be displayed after the interventional procedure is completed and after all impressions or notes are provided by the ultrasound operator. This end screen 364 indicates the exam is completed. This end screen 364 may further provide a summary of the images taken.

FIG. 4A depicts an example method 400 for facilitating performing a localization pre-surgical procedure using the disclosed ultrasound workflow tool. The method 400 may be performed by the ultrasound workflow tool executing on a wireless device having a processor, such as for example the system 100 and the operating environment 150. In one example, the ultrasound workflow tool facilitates operating the ultrasound device by providing step-by-step guidance for placing the localization device at or near the cancerous tissue. During the localization procedure, which is generally performed many hours before an excision or other surgical procedure, a localization device such as, for example, a wire, is placed at the lesion site. Thereafter, the localization device is used by a medical professional (generally a different medical professional) during the surgical procedure to guide an excision instrument to the cancerous tissue in order to excise cancerous tissue and a sufficient margin around the cancerous tissue. During the localization procedure, the medical professional locates the cancerous tissue by placing the ultrasound probe on the patient's breast to visually identify a previously implanted marker (e.g., implanted during a biopsy procedure) at the lesion site. Either a wire or wireless localization device is then placed at the site of the lesion and the marker. In some examples, however, a marker is not used.

The method 400 begins at operation 402 in which the ultrasound workflow tool displays a prompt to select a workflow from among a plurality of workflows. As described herein, the ultrasound workflow tool can facilitate various operations such as a diagnostic breast exam, an interventional procedure, and a localization procedure. In one example, a workflow is a sequence of predetermined steps that are performed during a particular procedure. In one example, the prompt displayed is a drop down menu or some other suitable menu used to select one of a plurality of workflows associated with a procedure.

At operation 404, the ultrasound workflow tool receives a selection of a localization workflow for a localization procedure. During a localization procedure, a localization device such as, for example, a wire, is placed at the lesion site, and is later used by the medical professional during a surgical procedure to guide an excision instrument to the cancerous tissue in order to excise cancerous tissue and a sufficient margin around the cancerous tissue. Accordingly, a localization procedure may be performed sometime after tissue excised from a biopsy is found to be malignant and before a surgical procedure to fully remove the cancerous tissue.

At operation 406, the ultrasound workflow tool receives one or more signals from the ultrasound device. In particular, in response to the medical professional performing the localization procedure to scan an anatomical feature of a patient using the ultrasound device, the ultrasound workflow tool receives one or more signals from the ultrasound device. In an example, the anatomical feature may be a patient's breast. Accordingly, the one or more signals may include one or more images of the patient's breast as the ultrasound device is used to scan the patient's breast during the localization procedure.

At operation 408, the ultrasound workflow tool causes display of an image of the scan. In one example, this may include a zoomed in image of the scan.

At operation 410, the ultrasound workflow tool identifies the cancerous tissue. In one example, the ultrasound workflow tool identifies cancerous tissue based on receiving a signal from the ultrasound probe in response to the medical professional's indication that the cancerous tissue is found using the ultrasound device. Alternatively or additionally, the ultrasound workflow tool may use image analysis or machine-learning techniques to automatically identify the cancerous tissue as the medical professional scans the patient's breast. In another example, the information from the diagnostic scan, such as the scan performed in steps described in reference to FIG. 2A, may be used to suggest an area where the cancerous tissue is located. This determination can be confirmed by the medical professional performing the localization procedure. The identified cancerous tissue may be displayed on a display of the wireless computing device on which the workflow tool application operates.

At operation 412, the ultrasound workflow tool evaluates the cancerous tissue to determine whether the identified cancerous tissue was previously characterized. As described herein, the localization procedure is performed sometime after performing an interventional procedure (e.g., a breast biopsy) to determine that a lesion is cancerous. Accordingly, in operation 412, the ultrasound workflow tool determines whether the cancerous tissue identified in the scan at operation 410 is the same lesion that was previously characterized as being cancerous after an interventional procedure. In one example, the cancerous tissue was not previously characterized, in which case the cancerous tissue may be newly developed or tissue that was not identified during a diagnostic scan or an interventional procedure. Alternatively, the cancerous tissue evaluated in operation 412 may have been previously identified and characterized in a diagnostic exam and tested after an interventional procedure. In some examples, the ultrasound workflow tool evaluates the size, location, shape, etc., of the identified cancerous tissue to make this determination.

At operation 414, the ultrasound workflow tool detects a first position of the localization device. In some examples, the localization device includes a transceiver having an RFID chip for providing orientation and location information. Accordingly, at operation 414, the ultrasound workflow tool detects the first position of the localization device based on one or more signals received from the RFID chip. In some examples, this first position is located within a region associated with the scanned anatomical feature.

At operation 416, the ultrasound workflow tool determines a first distance between the cancerous tissue and the localization device. In some examples, the site of the cancerous tissue may include a previously implanted marker. Accordingly, in some examples, the ultrasound workflow tool determines a distance from the localization device to the cancerous tissue (or to a marker implanted at the cancerous tissue). The ultrasound workflow tool can, in some examples, determine a distance between the cancerous tissue and the localization device based on knowledge of the respective locations.

At operation 418, the ultrasound workflow tool provides the calculated first distance between the localization device and the cancerous tissue (or marker implanted at the cancerous tissue). This calculated distance can be displayed on a screen of the ultrasound workflow tool operating on a wireless computing device. In aspects, the display may further indicate orientation information of the marker, the localization device, or both. Alternatively or additionally, the ultrasound workflow tool provides an audio signal specifying the calculated distance between the localization device and the cancerous tissue (or the implanted marker).

At operation 420, the ultrasound workflow tool determines if the localization device has moved. If, at operation 420, the ultrasound workflow tool determines that the localization device has not moved (NO at operation 420), the method 400 flows to operation 418. If the ultrasound workflow tool determines that the localization device has moved (YES at operation 420), the method 400 proceeds to operation 422 where the ultrasound workflow tool recalculates the distance between the localization device and the cancerous tissue (or the implanted marker).

At operation 424, the ultrasound workflow tool provides the recalculated distance computed in operation 422. This recalculated distance can be displayed on a screen of the ultrasound workflow tool operating on the wireless computing device. The display may further indicate orientation information of the marker, the localization device, or both. Alternatively or additionally, the ultrasound workflow tool provides voice guidance specifying the location of the cancerous tissue with reference to the location of the localization device. In one example, this voice guidance specifies the location of the cancerous tissue with reference to the localization device and the direction to which the medical professional should guide the localization device in order to ultimately place the localization device at or near the cancerous tissue. Accordingly, in some examples, the medical professional need only listen to voice guidance to determine how to guide the localization device to the cancerous tissue.

At operation 426, the ultrasound workflow tool determines whether the localization device is located at or near the cancerous tissue. As described, the ultrasound workflow tool determines the relative distance between the localization device and the cancerous tissue, and can therefore calculate when the localization device is located at the cancerous tissue. Alternatively or additionally, the ultrasound workflow tool provides an audio signal specifying the localization device is now located at the cancerous tissue. If the ultrasound workflow tool determines that the localization device is not located at or near the cancerous tissue (NO at operation 426) the method 400 flows to operation 420 to determine whether the localization device has moved. If the ultrasound workflow tool determines that the localization device is located at or near the cancerous tissue (YES at operation 426) the method 400 flows to operation 428.

At operation 428, the ultrasound workflow tool provides guidance to implant the localization device at the cancerous tissue site. In some examples, this guidance is a step-by-step instruction displayed on the display of the ultrasound workflow tool or some other display operatively connected to the ultrasound workflow tool. Alternatively or additionally, step-by-step audio instructions to implant the localization device are provided in operation 428.

Accordingly, with the aid of the ultrasound workflow tool, the medical professional does not need to rely solely on a rough visual interpretation of the location of the cancerous tissue and the boundaries thereof when placing the localization device at the site of the cancerous tissue. Furthermore, because the medical professional must hold the ultrasound device in one hand while placing a wire or wireless localization device with the other hand, the medical professional can use the hands-free workflow tool to facilitate locating and guiding the localization device to the cancerous tissue. With the workflow tool, significant time is saved and accuracy of determining placement is improved.

Although the method 400 discloses a particular sequence of operations, it is understood that these operations are exemplary, and therefore one or more of these operations may be optional or performed in a different sequence.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A computing device, comprising:
at least one processor configured to be communicatively coupled to an ultrasound probe operated by a user; and
at least one memory storing computer-executable instructions that implement an ultrasound workflow tool for facilitating a diagnostic procedure, the computer-executable instructions when executed by the at least one processor cause the computing device to:
provide a first prompt for selection of a workflow from among a plurality of workflows;
receive, from the user, a selection of a selected workflow from among the plurality of workflows;
receive one or more signals from the ultrasound probe operated by the user while scanning an anatomical feature of a patient;
detect, by the ultrasound workflow tool, a region of interest associated with the scanned anatomical feature;
during detection of the region of interest, cause display of the region of interest on a display of the computing device;
during display of the region of interest, provide a second prompt for classifying the detected region of interest;
receive from the user a classification of the region of interest in response to the second prompt provided by the computing device;
in response to receiving the classification, provide a template for identifying at least one location of the classified region of interest, wherein:
providing the template comprises providing a schematic representation of the anatomical feature,
the schematic representation comprising a first pictogram comprising a first two-dimensional line diagram of the anatomical feature, the first pictogram comprising a plurality of numerically identified circular regions that radiate from a nipple of the anatomical feature, wherein the anatomical feature is a breast, and
the schematic representation comprising a second pictogram, the second pictogram comprising a second two-dimensional line diagram of the anatomical feature, the second pictogram comprising a plurality of alphabetically identified regions that radiate from a top surface of the breast;
receive a first signal, in response to a first user selection on the first pictogram, of a location in relation to the nipple of the classified region of interest;
receive a second signal, in response to a second user selection on the second pictogram, of a depth of the classified region of interest;
translate the first user selection and the second user selection into number-letter coordinates identifying the at least one location of the classified region of interest;
provide a review screen on the display comprising one or more fields for characterizing the classified region of interest;
receive from the user a description into each of the one or more fields for characterizing the classified region of interest; and
generate a report of the diagnostic procedure based in part on the classified region of interest, the identified at least one location, and the received one or more descriptions.

2. The computing device of claim 1, wherein receiving the classification of the region of interest further comprises:
receiving an identification of the region of interest of at least one of a lesion or a cyst.

3. The computing device of claim 1, wherein the one or more fields for characterizing the classified region of interest comprise one or more of:
a readability finding;
a parenchymal pattern;
a focal lesion identification;
a size of the classified region of interest;
a margin of the classified region of interest;
a shape of the classified region of interest;
an echo pattern of the classified region of interest;
an orientation of the classified region of interest;
one or more posterior features of the classified region of interest;
one or more calcifications of the classified region of interest; and
one or more associated features of the classified region of interest.

4. The computing device of claim 1, the computer-executable instructions further causing the computing device to:
repeat the providing the second prompt and receiving the classification steps until the diagnostic procedure is complete.

5. The computing device of claim 1, wherein the providing the review screen step is performed immediately after completion of the diagnostic procedure.

6. The computing device of claim 1, wherein the generated report comprises a summary of the description received for each of the one or more fields characterizing the classified region of interest.

7. The computing device of claim 6, and wherein the generated report further comprises a pictogram of the breast, wherein the pictogram of the breast includes an identifier representing the detected region of interest.

8. The computing device of claim 1, wherein the selected workflow is a diagnostic workflow.

9. A method executed by a computing device having at least a display and a processor that implements a workflow tool for facilitating an ultrasound diagnostic procedure by a user during the ultrasound procedure, the method comprising:
providing a first prompt for selection of a workflow from among a plurality of workflows;
receiving, from the user, a selection of a selected workflow from among the plurality of workflows;
receiving one or more signals from an ultrasound probe scanning an anatomical feature of a patient during the ultrasound procedure;
detecting, by the ultrasound workflow tool, a region of interest associated with the scanned anatomical feature during the ultrasound procedure;

during detection of the region of interest, causing display of the region of interest on the display;

during display of the region of interest, providing a second prompt for classifying the detected region of interest;

receiving from the user a classification of the region of interest in response to the second prompt provided by the computing device;

in response to receiving the classification, providing a template for identifying at least one location of the classified region of interest, wherein:

providing the template comprises providing a schematic representation of the anatomical feature, the schematic representation comprising a first pictogram comprising a first two-dimensional line diagram of the anatomical feature, the first pictogram comprising a plurality of numerically identified circular regions that radiate from a nipple of the anatomical feature, wherein the anatomical feature is a breast, and the schematic representation comprising a second pictogram, the second pictogram comprising a second two-dimensional line diagram of the anatomical feature, the second pictogram comprising a plurality of alphabetically identified regions that radiate from a top surface of the breast;

receiving a first signal, in response to a first user selection on the first pictogram, of a location in relation to the nipple of the classified region of interest;

receiving a second signal, in response to a second user selection on the second pictogram, of a depth of the classified region of interest;

translating the first user selection and the second user selection into number-letter coordinates identifying the at least one location of the classified region of interest;

providing a review screen comprising one or more fields for characterizing the classified region of interest;

receiving from the user a description into each of the one or more fields for characterizing the classified region of interest; and generating a report of the diagnostic procedure based in part on the classified region of interest, the identified at least one location, and the received one or more descriptions.

\* \* \* \* \*